US006531316B1

(12) United States Patent
Patten et al.

(10) Patent No.: US 6,531,316 B1
(45) Date of Patent: Mar. 11, 2003

(54) ENCRYPTION OF TRAITS USING SPLIT GENE SEQUENCES AND ENGINEERED GENETIC ELEMENTS

(75) Inventors: Phillip A. Patten, Menlo Park, CA (US); Michael Lassner, Davis, CA (US)

(73) Assignee: MaxyAg, Inc., Redwood City, CA (US)

( * ) Notice: Subject to any disclaimer, the term of this patent is extended or adjusted under 35 U.S.C. 154(b) by 0 days.

(21) Appl. No.: 09/710,686

(22) Filed: Nov. 9, 2000

Related U.S. Application Data

(63) Continuation-in-part of application No. PCT/US00/05448, filed on Mar. 3, 2000, and a continuation-in-part of application No. PCT/US00/05573, filed on Mar. 3, 2000, and a continuation-in-part of application No. 09/517,933, filed on Mar. 3, 2000, now Pat. No. 6,365,377.
(60) Provisional application No. 60/122,943, filed on Mar. 5, 1999, provisional application No. 60/142,299, filed on Jul. 2, 1999, provisional application No. 60/164,617, filed on Nov. 10, 1999, and provisional application No. 60/164,618, filed on Nov. 10, 1999.

(51) Int. Cl.[7] .................. C12N 15/63; C12N 15/00; C12N 15/87; C12Q 1/68; C12P 19/34
(52) U.S. Cl. .................. 435/455; 435/6; 435/91.1; 435/440; 435/463
(58) Field of Search .................. 435/6, 91.1, 91.2, 435/91.32, 91.33, 91.4, 91.51, 7.2, 7.21, 7.31, 7.32, 455, 463, 464, 465, 470, 476, 483, 252.3, 320.1; 436/94; 536/23.1, 24.3, 24.33, 25.3

(56) References Cited

U.S. PATENT DOCUMENTS

| 5,512,463 A | 4/1996 | Stemmer |
| 5,514,588 A | 5/1996 | Varadaraj |
| 5,605,793 A | 2/1997 | Stemmer |
| 5,641,673 A | * 6/1997 | Haseloff et al. ............ 435/525 |
| 5,763,239 A | 6/1998 | Short et al. |
| 5,789,228 A | 8/1998 | Lam et al. |
| 5,811,238 A | 9/1998 | Stemmer et al. |
| 5,814,473 A | 9/1998 | Warren et al. |
| 5,824,469 A | 10/1998 | Horwitz et al. |
| 5,830,696 A | 11/1998 | Short |

(List continued on next page.)

FOREIGN PATENT DOCUMENTS

| EP | 0911396 A2 | 4/1999 |
| EP | 0911396 A3 | 5/1999 |
| EP | 0934999 A1 | 8/1999 |
| WO | WO 97/07205 | 2/1997 |
| WO | WO 97/20078 | 6/1997 |
| WO | WO 97/25410 | 7/1997 |
| WO | WO 97/35957 | 10/1997 |

(List continued on next page.)

OTHER PUBLICATIONS

Wu et al., Protein trans–splicing by a split intein encoded in a split DnaE gene of Synechocystis sp. PCC6803. Proc. Natl. Acad. Sci., USA, 9226–9231, Aug. 1998.*

(List continued on next page.)

Primary Examiner—Ethan C. Whisenant
Assistant Examiner—Frank Lu
(74) Attorney, Agent, or Firm—Christopher M. Holman; Norman J. Kruse

(57) ABSTRACT

Methods of unencrypting trait encrypted gene sequences to provide unencrypted RNAs or polypeptides. The invention also relates to methods of encrypting traits including splitting genes between two parental organisms or between a host organism and a vector. The gene sequences are unencrypted when the two parental organisms are mated or when the vector infects the host organism by trans-splicing either the split RNAs or split polypeptides upon expression of the split gene sequences. The invention also includes methods of providing multiple levels of trait encryption and reliable methods of producing hybrid organisms. Additional methods include those related to unencrypting engineered genetic elements to provide polypeptide functions and those directed at recombining non-overlapping gene sequences. The invention also includes integrated systems and various compositions related to the disclosed methods.

41 Claims, 8 Drawing Sheets

U.S. PATENT DOCUMENTS

Figure 2:
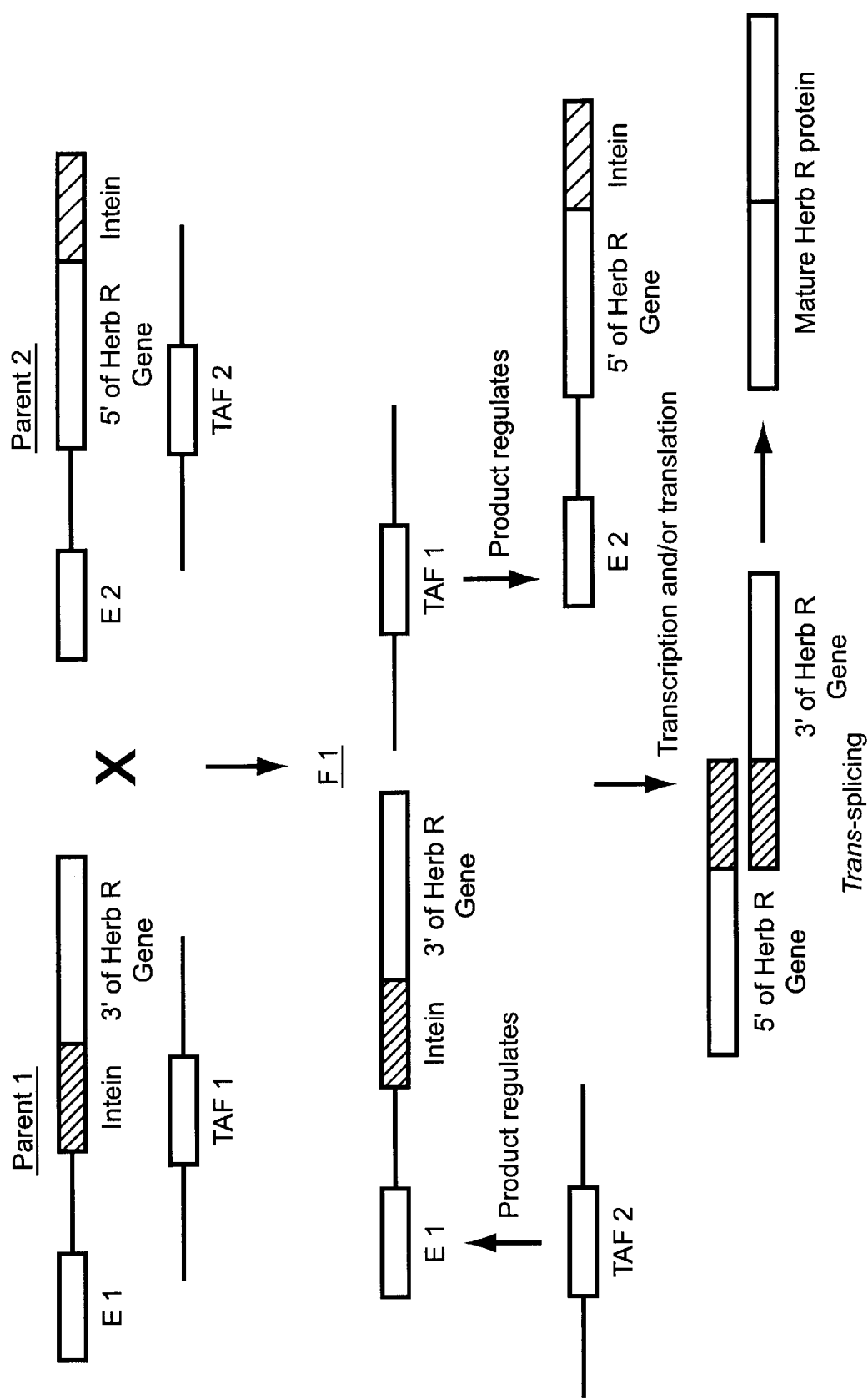

| | | |
|---|---|---|
| 5,830,721 A | 11/1998 | Stemmer et al. |
| 5,834,252 A | 11/1998 | Stemmer et al. |
| 5,837,458 A | 11/1998 | Minushull et al. |
| 5,866,363 A | 2/1999 | Pieczenik |
| 5,876,997 A | 3/1999 | Kretz |
| 5,925,749 A | 7/1999 | Mathur et al. |
| 5,928,905 A | 7/1999 | Stemmer et al. |
| 5,939,250 A | 8/1999 | Short |
| 5,939,300 A | 8/1999 | Robertson et al. |
| 5,942,430 A | 8/1999 | Robertson et al. |
| 5,948,666 A | 9/1999 | Callen et al. |
| 5,958,672 A | 9/1999 | Short |
| 5,958,751 A | 9/1999 | Murphy et al. |
| 5,962,258 A | 10/1999 | Mathur et al. |
| 5,962,283 A | 10/1999 | Warren et al. |
| 5,965,408 A | 10/1999 | Short |
| 5,985,646 A | 11/1999 | Murphy et al. |
| 6,001,574 A | 12/1999 | Short et al. |
| 6,004,788 A | 12/1999 | Short |
| 6,030,779 A | 2/2000 | Short |
| 6,054,267 A | 4/2000 | Short |
| 6,096,548 A | 8/2000 | Stemmer |
| 6,117,679 A | 9/2000 | Stemmer |
| 6,132,970 A | 10/2000 | Stemmer |

FOREIGN PATENT DOCUMENTS

| | | |
|---|---|---|
| WO | WO 97/35966 | 10/1997 |
| WO | WO 97/44361 | 11/1997 |
| WO | WO 97/48416 | 12/1997 |
| WO | WO 97/48717 | 12/1997 |
| WO | WO 97/48794 | 12/1997 |
| WO | WO 98/00526 | 1/1998 |
| WO | WO 98/01581 | 1/1998 |
| WO | WO 98/13485 | 4/1998 |
| WO | WO 98/13487 | 4/1998 |
| WO | WO 98/24799 | 6/1998 |
| WO | WO 98/27230 | 6/1998 |
| WO | WO 98/24816 | 7/1998 |
| WO | WO 98/31837 | 7/1998 |
| WO | WO 98/36080 | 8/1998 |
| WO | WO 98/41622 | 9/1998 |
| WO | WO 98/41623 | 9/1998 |
| WO | WO 98/41653 | 9/1998 |
| WO | WO 98/42832 | 10/1998 |
| WO | WO 98/48034 | 10/1998 |
| WO | WO 98/58085 | 12/1998 |
| WO | WO 99/07837 | 2/1999 |
| WO | WO 99/08539 | 2/1999 |
| WO | WO 99/10472 | 3/1999 |
| WO | WO 99/10539 | 3/1999 |
| WO | WO 99/19518 | 4/1999 |
| WO | WO 99/21979 | 5/1999 |
| WO | WO 99/23107 | 5/1999 |
| WO | WO 99/23236 | 5/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/45154 | 9/1999 |
| WO | WO 99/57128 | 11/1999 |
| WO | WO 99/65927 | 12/1999 |
| WO | WO 00/42560 | 7/2000 |
| WO | WO 00/42561 | 7/2000 |
| WO | WO 00/53744 | 9/2000 |
| WO | WO 00/58517 | 10/2000 |

OTHER PUBLICATIONS

Shingledecker et al., Molecular dissection of the Myobacterium tuberculosis RecA intein: design of a minimal intern and of a trans–splicing system involving two intein fragments. Gene, 207, 187–195, Jan. 1998.*

Eul et al., Experimental evidence for RNA trans–splicing in mammalian cells. EMBO. J., 14, 3226–3234, 1995.*

Ghetti et al., In vitro trans–splicing in *Saccharomyces cerevisae*Proc. Natl. Acad. Sci. USA, 92, 11461–11464, Dec. 1995.*

Pereira de Souza et al., A trans splicing model for the expression of the tripartite nad5 gene in wheat and maize mitochondria. The Plant Cell., 3, 1363–1378, Dec. 1991.*

Knoop et al., Trans splicing integrates an exon of 22 nucleotides into the nad5 mRNA in higher plant mitochondria. EMBO J., 10, 3483–3493, 1991.*

Caudevilla et al., Natural trans splicing in carniture octanoyltransferase pre–mRNAs in rat liverProc. Natl. Acad. Sci., USA, 12185–12190, Oct. 1998.*

Chang, C., et al. (1999) "Evolution of a cytokine using DNA family shuffling." *Nature Biotechnology* 17:793–797.

Christians, F.C. et al., (1999) "Directed evolution of thymidine kinase for AZT phosphorylation using DNA family shuffling." *Nature Biotechnology* 17:259–264.

Crameri et al., (1993) "10(20)–Fold aptamer library amplification without gel purification," *Nuc. Acids Res.* 21(18):4410.

Crameri, A. & Stemmer W.P.C. (1995) "Combinatorial multiple cassette mutagenesis creates all the permutations of mutant and wildtype cassettes." *Biotechniques* 18:194–195.

Crameri, A. et al. (1996) "Improved green fluorescent protein by molecular evolution using DNA shuffling." *Nature Biotechnology* 14:315–319.

Crameri, A. et al. (1996) "Construction and evolution of antibody–phage libraries by DNA shuffling." *Nature Medicine* 2:100–103.

Crameri, A. et al., (1997) "Molecular evolution of an arsenate detoxification pathway by DNA shuffling." *Nature Biotechnology* 15:436–438.

Crameri, A. et al., (1998) "DNA shuffling of a family of genes from diverse species accelerates directed evolution." *Nature* 391:288–291.

Gates, C.M. et al., (1996) "Affinity selective isolation of ligands from peptide libraries through display on a lac repressor headpiece dimer". *Journal of Molecular Biology* 255:373–386.

Minshull, J. Stemmer, W.P.C. (1999) "Protein evolution by molecular breeding." *Current Opinion in Chemical Biology* 3:284–290.

Ness, J. et al., (1999) "DNA shuffling of subgenominc sequences of subtilisin." *Nature Biotechnology* 17:893–896.

Patten, P.A. et al., (1997) "Application of DNA Shuffling to Pharmaceuticals and Vaccines." *Current Opinion in Biotechnology* 8:724–733.

Stemmer, W.P.C. (1994) "DNA Shuffling by random fragmentation and reassembly: In vitro recombination for molecular evolution." *PNAS* 91:10751.

Stemmer, W.P.C. (1994) "Rapid evolution of a protein in vitro by DNA shuffling." *Nature* 370:389–391.

Stemmer, W.P.C. (1995) "The Evolution of Molecular Computation." *Science* 270:1510.

Stemmer, W.P.C. (1995) "Searching Sequence Space." *Bio/Technology* 13:549–553.

Stemmer, W.P.C. (1996) "Sexual PCR and Assembly PCR." In: *The Encyclopedia of Molecular Biology*. VCH Publishers, New York. pp. 447–457.

Stemmer, W.P.C. & Soong, N.W. (1999) "Molecular breeding of viruses for targeting and other clinical properties." *Tumor Targeting* 4:59–62.

Zhang, J. et al., (1997) "Directed evolution of an effective fucosidase from a galactosidase by DNA shuffling and screening." *Proceedings of the National Academy of Sciences, USA* 94:4504–4509.

* cited by examiner

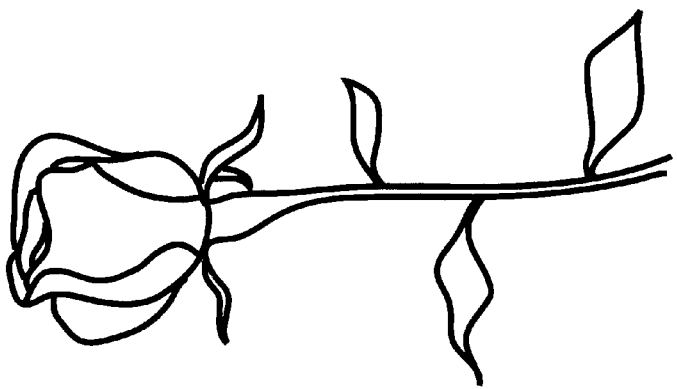
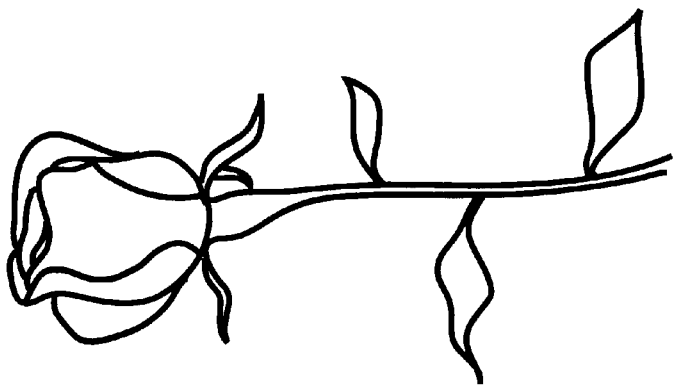
Fig. 1

A

| | |
|---|---|
| Ssp | (633 aa)-FQLESQGMKQIVRDLKPSGIEDISSILALYRPGPLDAG |
| Eco | (608 aa)-FQLESRGMKDLIKRLQPDCFEDMIALVALFRPGPLQSG |
| Bsu | (584 aa)-FQLESAGMRSVLKRLKPSGLEDIVAVNALYRPGPMEN- |
| Mtu | (636 aa)-FQLDGGPMRDLLRRMQPTGFEDVVAVIALYRPGPMGMN |
| | ***.   *. ... ..*   . ..  .****. |

| | |
|---|---|
| Ssp | LIPIFINRKHGRE-----EISYQHKLLEPILNETYGVLVYQEQIMKM |
| Eco | MVDNFIDRKHGREEISYPDVQWQHESLKPVLEPTYGIILYQEQVMQI |
| Bsu | -IPLFIDRKHGRA-----PVHYPHEDLRSILEDTYGVIVYQEQIMMI |
| Mtu | AHNDYADRKNNRQ-AIKPIHPELEEPLREILAETYGLIVYQEQIMRI |
| | . **..*          * .* *...**.* . |

| | |
|---|---|
| Ssp | AQDLADYSLGEADLLRRAMGKKKAEEMQKHRAKFVDGSTKHGVPSRI |
| Eco | AQVLSGYTLGGADMLRRAMGKKKPEEMAKQRSVFAEGAEKNGINAEL |
| Bsu | ASRMAGFSLGEADLLRRAVSKKKKEILDRERSHFVEGCLKKEYSVDT |
| Mtu | AQKVASYSLARADILRKAMGKKKREVLEKEFEGFSDGMQANGFSPAA |
| | *   .. ..*  ..*. ***  *  . .      * .* |

| | |
|---|---|
| Ssp | AENLFDQMVKFAEY[Int-n] [Int-c]CFNKSHSTAYA |
| Eco | AMKIFDLVEKFAGY----------------------GFNKSHSAAYA |
| Bsu | ANEVYDLIVKFANY----------------------GFNRSHAVAYS |
| Mtu | IKALWDIILPFADY----------------------AFNKSHAAGYG |
| | . *  .. ** *                         .. * |

| | |
|---|---|
| Ssp | YVTYQTAYLKANYPVEYMAALLTASSDSQEKVEKYRENCQKMGITVE |
| Eco | LVSYQTLWLKAHYPAEFMAAVMTADMDNTEKVVGLVDECWRMGLKIL |
| Bsu | MIGCQLAYLKAHYPLYFMCGLLTSVIGNEDKISQYLYEAKGSGIRIL |
| Mtu | MVSYWTAYLKANYPAEYMAGLLTSVGDDKDKAAVYLADCRKLGITVL |
| | .   *. .*...*.   .*     .   *.. |

| | |
|---|---|
| Ssp | PPDINRSQRHFTPLG-EAILFGLSAVRNLGEGAIEQIITARDNSEEK |
| Eco | PPDINSGLYHFHVNDDGEIVYGIGAIKGVGEGPIEAIIEARN--KGG |
| Bsu | PPSVNKSSFPFTVEN-GSVRYSLRAIKSVGVSAVKDIYKAR---KEK |
| Mtu | PPDVNESGLNFASVG-QDIRYGLGAVRNVGANVVGSLLQTRN--DKG |
| | ** .*   *       ...*...*   . ..* |

| | |
|---|---|
| Ssp | RFKSLADFCTQVDLRVVNRRAIETLIMAGAFD-(286 aa) |
| Eco | YFRELFDLCARTDTKKLNRRVLEKLIMSGAFD-(271 aa) |
| Bsu | PFEDLFDFCFRVPSKSVNRKMLEALIFSGAMD-(201 aa) |
| Mtu | KFTDFSDYLNKIDISACNKKVTESLIKAGAFD-(269 aa) |
| | *    *    .   *.. * ** .** * |

B

```
                                Int-n
                              ┌─►
                              │ *
      Ssp DnaE    CLSFGTEILTVEY
      Rma DnaB    CLAGDTLITLAD-
      Ssp DnaB    CISGDSLISLAST
      Ppu DnaB    CISKFSHIMWSHV
                    Block A Ssp DnaE    GRVYTQAIAQWHI
      Rma DnaB    YRLERARVSRAFC
      Ssp DnaB    MKLESAKVSRVFC
      Ppu DnaB    YQLLDQGEAFISF Ssp DnaE    LTTDYQLLAIEEI
      Rma DnaB    LTPQG-WKRVDEL
      Ssp DnaB    LTIDG-WKRLDEL
      Ppu DnaB    LTLRG-WQRCDQL Ssp DnaE    LPFPLLDAGTIK
      Rma DnaB    AELALLGHLIGD-
      Ssp DnaB    EELGLLGHLIGD-
      Ppu DnaB    IPFSLCNFET---

Ssp DnaE    RIFDIGLPQDHNF
      Rma DnaB    EVFDLTVPGPHNF
      Ssp DnaB    EVFDLTVPGPHNF
      Ppu DnaB    NVFDFAANPIPNF
                    Block F
```

Fig. 6

ENCRYPTION OF TRAITS USING SPLIT GENE SEQUENCES AND ENGINEERED GENETIC ELEMENTS

CROSS-REFERENCES TO RELATED APPLICATIONS

This application is related to USSN60/122,943 "RECOMBINATION OF INSERTION MODIFIED NUCLEIC ACIDS" by Patten et al., filed Mar. 5, 1999; USSN 60/142,299 "RECOMBINATION OF INSERTION MODIFIED NUCLEIC ACIDS" by Patten et al., filed Jul. 2, 1999; USSN60/164,617 "RECOMBINATION OF INSERTION MODIFIED NUCLEIC ACIDS" by Patten et al., filed Nov. 10, 1999; U.S. Ser. No. 09/517,933 "RECOMBINATION OF INSERTION MODIFIED NUCLEIC ACIDS" by Patten et al., filed Mar. 3, 2000; now U.S. Pat. No. 6,365,377 and PCT/US00/05573 "RECOMBINATION OF INSERTION MODIFIED NUCLEIC ACIDS" by Patten et al., filed Mar. 3, 2000. This application is also related to USSN60/164,618 "ENCRYPTION OF TRAITS USING SPLIT GENE SEQUENCES AND ENGINEERED GENETIC ELEMENTS" by Patten et al., filed Nov. 10, 1999 and PCT/US00/05448 "ENCRYPTION OF TRAITS USING SPLIT GENE SEQUENCES AND ENGINEERED GENETIC ELEMENTS" by Patten et al., filed Mar. 3, 2000. The disclosures of each of these related applications are incorporated by reference. The present application claims priority to and the benefit of each of these related applications, pursuant to 35. U.S.C. 119(e) and 120, as appropriate.

FIELD OF THE INVENTION

The present invention provides methods of encrypting traits, including, e.g., splitting genes between two parental organisms or between a host organism and a vector. The invention also relates to methods of unencrypting trait encrypted gene sequences to provide unencrypted RNAs or polypeptides. Gene sequences are unencrypted when the two parental organisms are mated, or when the vector infects the host organism by trans-splicing either the split RNAs, or the split polypeptides upon expression of the split gene sequences. The invention also includes methods of providing multiple levels of trait encryption and reliable methods of producing hybrid organisms. Additional methods include those directed at unencrypting engineered genetic elements to provide unencrypted polypeptide functions and those related to recombining non-overlapping gene sequences. Furthermore, the present invention includes integrated systems and various compositions related to the methods disclosed herein.

BACKGROUND OF THE INVENTION

Intermolecular splicing is termed trans-splicing. The mechanism of splicing two independently transcribed pre-mRNAs was discovered in trypanosomes. Murphy, W. J. et al. (1986) *Cell* 47, 517–525 and Sutton, R. and Boothroyd, J. C. (1986) *Cell* 47, 527–535. Thereafter, trans-splicing was also described in other organisms, e.g., *C. elegans* (Krause, M. and Hirsch, D. (1987) *Cell* 49, 753–761, Huang, X. Y. and Hirsch, D. (1989) *Proc. Nat. Acad. Sci. USA* 86, 8640–8644, and Hannon, G. J. et al. (1990) *Cell* 61, 1247–1255), *Schistosoma mansoni* (Rajkovic, A., et al. (1990) *Proc. Nat. Acad. Sci. USA* 87, 8879–8883 and Davis, R. E. et al. (1995) *J. Biol. Chem.* 270, 21813–21819), and plant mitochondria (Malek, O. et al. (1997) *Proc. Nat. Acad. Sci. USA* 94, 553–558). Targeted trans-splicing has been demonstrated in HeLa nuclear extracts, in cultured H1299 human lung cancer cells, and in H1299 tumor bearing athymic mice. Puttaraju, M. et al. (1999) *Nat. Biotech.* 17, 246–252. Suggested practical applications of targeted trans-splicing are, e.g., as a means for gene therapy. Id.

Various ribozymes capable of precisely trans-splicing, either in vitro or in vivo, exon sequences into target RNA sequences have been described in, e.g., Haseloff et al., U.S. Pat. No. 5,882,907 "CELL ABLATION USING TRANS-SPLICING RIBOZYMES," Haseloff et al., U.S. Pat. No. 5,874,414 "TRANS-SPLICING RIBOZYMES," Haseloff et al., U.S. Pat. No. 5,866,384 "CELL ABLATION USING TRANS-SPLICING RIBOZYMES," Haseloff et al., U.S. Pat. No. 5,863,774 "CELL ABLATION USING TRANS-SPLICING RIBOZYMES," Haseloff et al., U.S. Pat. No. 5,849,548 "CELL ABLATION USING TRANS-SPLICING RIBOZYMES," and Haseloff et al., U.S. Pat. No. 5,641,673 "CELL ABLATION USING TRANS-SPLICING RIBOZYMES." Methods of ablating cells in vivo involving targeted trans-splicing to provide toxic products that generate sterile plants have also been described in, e.g., Haseloff et al., U.S. Pat. No. 5,866,384, supra. The techniques referenced above generally involve trans-splicing RNA sequences into native target RNAs.

Genetically male-sterile plants can be desirable for the production of hybrid seeds, because they avoid the need for expensive and laborious removal of, e.g., anthers from flowers to prevent self-fertilization. Transgenic methods of regenerating functionally male-sterile plants have included the development of pollen cells that are ablated specifically by the expression of fungal or bacterial ribonuclease transgenes fused to a pollen-specific promoter from the particular plant. Mariani, C. et al. (1992) *Nature* 357, 384–387. See also, Haseloff et al., U.S. Pat. No. 5,866,384, supra.

In addition to trans-splicing RNAs, protein trans-splicing is also known. For example, certain modified proteins have been described which include "controllable intervening protein sequences" inserted into or adjacent to target proteins. Comb, et al. U.S. Pat. No. 5,834,247 "MODIFIED PROTEINS COMPRISING CONTROLLABLE INTERVENING PROTEIN SEQUENCES OR THEIR ELEMENTS METHODS OF PRODUCING SAME AND METHODS FOR PURIFICATION OF A TARGET PROTEIN COMPRISED BY A MODIFIED PROTEIN." The inserted intervening sequences are capable of cleaving the modified protein in trans under controllable conditions, e.g., increased temperature, exposure to light, treatment with chemical reagents, etc. Furthermore, these intervening protein sequences can also be inserted into a target protein sequence so as to render the target inactive. Id. See also, Comb, et al. U.S. Pat. No. 5,496,714 "MODIFICATION OF PROTEIN BY USE OF A CONTROLLABLE INTERVENING PROTEIN SEQUENCE" and Belfort, U.S. Pat. No. 5,795,731 "INTEINS AS ANTIMICROBIAL TARGETS: GENETIC SCREENS FOR INTEIN FUNCTION." Spontaneous (native) trans-splicing of both inteins and RNAs is also known.

More generally, relevant features of inteins and intein splicing, as well as certain forms of chemical ligation of polypeptides, are described in the abundant literature on the topics, including the references noted above and, e.g.: Clarke (1994) "A proposed mechanism for the self-splicing of proteins" *Proc. Natl. Acad. Sci. USA* 91:11084–11088; Clyman (1995) "Some Microbes have splicing proteins" *ASM News* 61:344–347; Colston and Davis (1994) "The ins and outs of protein splicing elements" *Molecular Microbiology* 12, 359–363; Cooper et al. (1993) "Protein splicing of the yeast TFP1 intervening protein sequence: a model for self-excision" *EMBO J.* 12:2575–2583; Cooper and Stevens (1993) "Protein splicing: Excision of intervening sequences at the protein level" *BioEssays* 15, 667–673; Cooper and Stevens (1995) "Protein splicing: Self-splicing of genetically mobile elements at the protein level" *TIBS* 20, 351–357; Cook et al. (1995) "Photochemically initiated protein splicing" *Angew. Chem. Int. Ed. Engel* 34, 1620–1630; Dalgaard, J. (1994) "Mobile introns and inteins: friend or foe?" *Trends Genet* 10, 306–7; Davis et al. (1992) "Protein Splicing in the Maturation of M. Tuberculosis RecA Protein: A Mechanism for Tolerating a Novel Class of Intervening Sequence" *Cell* 71:201–210; Davis et al. (1991) "Novel Structure of the recA Locus of *Mycobacterium tuberculosis* Implies Processing of the Gene Product" *J. Bacteriol.* 173:5653–5662; Davis et al. (1994) "Evidence of selection for protein introns in the RecAs of pathogenic Mycobacteria" *EMBO J.* 13, 699–703; Davis et al. (1995) "Protein splicing—the lengths some proteins will go to" *Antonie Van Leeuwenhoek* 67:131–137; Doolittle, (1993) "The comings and goings of homing endonucleases and mobile introns" *Proc. Natl. Acad. Sci. USA.* 90:5379–5381; Doolittle and Stoltzfus (1993) "Genes-in-pieces revisited" *Nature* 361:403; Hirata and Anraku (1992) "Mutations at the Putative Junction Sites of the Yeast VMA1 Protein, the Catalytic Subunit of the Vacuolar Membrane H+–ATPase, Inhibit its Processing by Protein Splicing" *Biochem. Biophys. Res. Comm.* 188:40–47; Hirata et al. (1990) "Molecular Structure of a Gene, VMA1, Encoding the Catalytic Subunit of H+–Translocating Adenosine Triphosphatase from Vacuolar Membranes of *Saccharomyces cereviaiae" J. Biol. Chem.* 265, 6726–6733; Hodges et al. (1992) "Protein splicing removes intervening sequences in an archaea DNA polymerase" *Nucleic Acids Res.* 20:6153–6157; Kane et al. (1990) "Protein Splicing Converts the Yeast TFP1 Gene Product to the 69-kD Subunit of the Vacuolar H+–Adenosine Triphosphatase" *Science* 250:651–657; Koonin (1995) "A protein splice-junction motif in hedgehog family proteins" *Trends Biochem. Sci.* 20:41–142; Kumar et al. (1996) "Functional characterization of the precursor and spliced forms of recA protein of *Mycobacterium tuberculosis" Biochemistry* 35:1793–1802, and Kawasaki, M., et al., Biochemical and Biophysical Research Communications, vol. 222, "Folding-dependent in vitro protein splicing of the *Saccharomyces cerevisiae* VMA1 protozyme", pp. 827–832, 1996. Gimble and Thorner (1992) *Nature* 357:301–306; Gimble and Thorner (1993) *J. Biol. Chem.,* 268:21844–21853; Pietrovski (1996) "A new intein in cyanobacteria and its significance for the spread of inteins" *Trends in Genetics* 12:287–288; Shao et al. (1996) "Proteins splicing: Evidence for an N—O acyl rearrangement as the initial step in the splicing process" *Biochemistry,* 35:3810–3815; Shub and Goodrich-Blair (1992) *Cell,* 71:183–186; WO 98/49274; WO 98/49275; WO 98/40394; WO 99/11655; WO 96/34878; WO 98/28434; Kent et al. U.S. Pat. No. 5,910,437; Dawson et al. U.S. Pat. No. 5,891,993; and Jocbs et al., U.S. Pat. No. 5,981,182. Additional details on protein splicing generally can be found at the Intein Databases web site (www.neb.com/neb/inteins/intein_intro.html); and in, e.g., *Nucleic Acids Research* 26(7):1741–1758.

Methods of encrypting gene sequences and engineered genetic elements, and additional recombination methods would be desirable. The present invention provides new methods to encrypt traits including trans-splicing at the RNA and/or protein levels, and new methods of recombining non-overlapping gene sequences, as well as a variety of additional features which will become apparent upon complete review of the following description.

SUMMARY OF THE INVENTION

The present invention provides methods of unencrypting trait encrypted gene sequences, e.g., cDNAs, to provide unencrypted RNAs or polypeptides, e.g., full-length proteins. The methods include providing a first plurality of split gene sequences in which each split gene sequence includes a subsequence of a genetic element and transcribing the first plurality of split gene sequences to provide a plurality of RNA segments that can include trans-splicing introns. The steps of this aspect of the invention can occur either in vitro or in vivo. Two or more of the plurality of RNA segments can be trans-spliced together to provide an unencrypted RNA. The unencrypted RNA is optionally -selected for a desired trait or property, or translated to provide a second unencrypted polypeptide. The second unencrypted polypeptide is also optionally selected for a desired trait or property.

Alternately, the plurality of RNA segments can be translated to provide a plurality of polypeptide segments that can include trans-splicing inteins and two or more of that plurality can be trans-spliced together to provide a first unencrypted polypeptide. The first unencrypted polypeptide is optionally selected for at least one desired trait or property.

The first plurality of split gene sequences is optionally provided by mating a first parental organism that includes a second plurality of split gene sequences with a second parental organism that includes a third plurality of split gene sequences to produce a progeny organism. The progeny organism includes one or more of both the second and the third plurality of split gene sequences. Thereafter, one or more of the second and the third plurality of split gene sequences can be transcribed to provide a plurality of RNA segments. Additionally, the progeny organism is optionally selected for a desired trait or property, and in so doing, unencrypted RNAs are selected. The unencrypted RNAs are optionally translated to provide an unencrypted polypeptide. The unencrypted polypeptides are optionally selected for a desired trait or property. The first and second parental organisms of this aspect of the present invention can be, e.g., animals, plants, fungi, or bacteria. In certain preferred embodiments they are plants, yeast or other fungi.

A first parental organism can include a first plurality of enhancer-linked split gene sequences. Each enhancer-linked split gene sequence includes a subsequence of a genetic element with a first enhancer sequence linked thereto. The first parental organism also includes one or more first trans-acting transcription factor sequences that are unlinked to the first plurality of enhancer-linked split gene sequences. This aspect of the invention also includes a second parental organism that includes a second plurality of enhancer-linked split gene sequences in which each enhancer-linked split gene sequence includes a subsequence of the genetic element with a second enhancer sequence linked thereto. The second parental organism also includes one or more second trans-acting transcription factor sequences that are unlinked to the second plurality of enhancer-linked split gene sequences.

The two parental organisms are optionally mated to produce a progeny organism that includes the first and the second plurality of enhancer-linked split gene sequences and the first and the second trans-acting transcription factor sequences. The first and the second plurality of enhancer-linked split gene sequences can be transcribed to provide a plurality of RNA segments in which the first plurality of enhancer-linked split gene sequences are regulated by a second trans-acting transcription factor and the second plurality of enhancer-linked split gene sequences are regulated by a first trans-acting transcription factor. The progeny organism is optionally selected for a desired trait or property. Unencrypted RNAs are optionally translated to provide unencrypted polypeptides that, in turn, can be selected for a desired trait or property. Furthermore, the first and second parental organisms can be, e.g., animals, plants, fungi, or bacteria. However, in certain preferred embodiments they are plants, yeast or other fungi.

A first parental organism can include a second plurality of split gene sequences in which each split gene sequence includes a subsequence of a toxic genetic element and a second parental organism can include a third plurality of split gene sequences in which each split gene sequence also includes a subsequence of the toxic genetic element. The first and second parental organisms of this aspect of the invention can be mated and the second and third plurality of split gene sequences can be expressed in a progeny organism to produce a second and third plurality of polypeptide sequences. Thereafter, one or more of the second and third plurality of polypeptide sequences can be trans-spliced together to provide a toxic polypeptide. The toxic polypeptide, in turn, renders the progeny organism incapable of reproducing when it is male. However, the progeny organism can reproduce when it is female and when it does, the progeny organism produces hybrid progeny organisms in which the toxic genetic element is not expressed.

A toxic polypeptide can render the progeny organism incapable of reproducing when it is female. However, this progeny organism is capable of reproducing when it is male and when it does, the progeny organism produces hybrid progeny organisms in which the toxic genetic element is not expressed.

In another embodiment of the present invention, a first plurality of split gene sequences is provided by infecting a host organism that includes a second plurality of split gene sequences with a vector, e.g., a virus, that includes a third plurality of split gene sequences to produce an infected organism. The infected organism includes the second and third plurality of split gene sequences. The second and third plurality of split gene sequences can be transcribed to provide a plurality of RNA segments. Additionally, an unencrypted RNA is optionally selected for a desired trait or property, or a second unencrypted RNA can be translated to provide a second unencrypted polypeptide. The first or second unencrypted polypeptides are optionally selected for a desired trait or property.

The present invention also provides methods of unencrypting engineered genetic elements to provide unencrypted polypeptide functions that can occur in vitro or in vivo. This method includes providing a first engineered genetic element, e.g., a cDNA, which corresponds to an encoded first polypeptide, e.g., an engineered biotin ligase that is functional. It also includes providing a second engineered genetic element that corresponds to an encoded second polypeptide, e.g., an engineered biotin dependent glyphosate resistance polypeptide, that is nonfunctional in the absence of a modification performed by the first polypeptide. Thereafter, the first and second engineered genetic elements can be mixed and expressed to produce the encoded first and second polypeptides. The encoded first polypeptide then modifies the encoded second polypeptide to provide a functional encoded second polypeptide.

In an embodiment of the methods of unencrypting engineered genetic elements, the providing and mixing steps include mating a first parental organism that includes the first engineered genetic element and a second parental organism that includes the second engineered genetic element to produce a progeny organism that includes both engineered genetic elements. Thereafter, the genetic elements in the progeny organism can be expressed to produce the encoded first and second polypeptides. The first and second parental organisms of this aspect of the invention can be, e.g., animals, plants, fungi, or bacteria. In certain preferred embodiments they are plants, yeast or other fungi.

The providing and mixing steps, of the methods of unencrypting engineered genetic elements, optionally include infecting a host organism that includes the first engineered genetic element with a vector that includes the second engineered genetic element to produce an infected organism. Alternatively, the vector can include the first engineered genetic element and the host organism can include the second engineered genetic element. In either case, the infected organism ultimately includes both the first and the second engineered genetic elements. Thereafter, both engineered genetic elements can be expressed in the progeny organism to produce the encoded first and second polypeptides.

The present invention also provides a composition that includes libraries of two or more populations (e.g., homologous genetic elements) of split gene sequences. These libraries collectively include a plurality of split gene sequence member types in which combinations or subcombinations of those member types collectively correspond to one or more complete genetic elements.

The invention additionally provides a composition that includes libraries of two or more populations of enhancer-linked split gene sequences. These libraries collectively include a plurality of enhancer-linked split gene sequence member types, each regulated by a different trans-acting transcription factor in which combinations or subcombinations of the plurality of enhancer-linked split gene sequence member types collectively correspond to one or more complete genetic elements. This composition can include a trans-acting transcription factor corresponding to one of the two or more populations of enhancer-linked split gene sequences that can regulate the enhancer-linked split gene sequences of another population. This composition can also include a first trans-acting transcription factor that corresponds to a first population of enhancer-linked split gene sequences that regulates the enhancer-linked split gene sequences of a second population, and a second trans-acting transcription factor that corresponds to the second population of enhancer-linked split gene sequences that regulates the enhancer-linked split gene sequences of the first population.

The present invention also relates to methods of recombining non-overlapping gene sequences that can occur in vitro or in vivo. The methods include providing a plurality of non-overlapping gene sequences in which each non-overlapping gene sequence corresponds to a different subsequence of a genetic element. The methods also include providing a plurality of gap nucleic acid sequences in which each gap nucleic acid sequence overlaps two or more of the non-overlapping gene sequences. The non-overlapping gene sequences can be recombined with the gap nucleic acid sequences to provide recombined non-overlapping gene sequences. The recombined non-overlapping gene sequences are optionally selected for a desired trait or property and then recombined again. This process of selecting and recombining the recombined non-overlapping gene sequences can be repeated until a desired recombined genetic element is obtained. Furthermore, the plurality of non-overlapping gene sequences can be derived, e.g., from a cry3Bb gene and the plurality of gap nucleic acid sequences can be derived, e.g., from a cry1Ba, a cry1Ca, and a cry1Ia gene.

The present invention is also directed at compositions that include libraries of gap nucleic acids. The libraries of gap nucleic acids include a plurality of gap nucleic acid member types in which each gap nucleic acid member type includes subsequence identity or complementarity with at least two split gene sequence member types.

The invention additionally provides an integrated system that includes a computer or computer readable medium that includes a data set corresponding to a set of character strings. Those character strings can correspond to split gene sequences, enhancer-linked split gene sequences, trans-acting transcription factor sequences, engineered genetic elements, non-overlapping gene sequences and gap nucleic acids. The system can further include a sequence search and comparison instruction set for searching for specified nucleic acid sequences. The integrated system also optionally includes an automatic sequencer and/or synthesizer coupled to an output of the computer or computer readable medium, which can accept instructions from the computer or computer readable medium that direct the sequencing and/or synthesis of selected sequences.

The integrated system optionally includes robotic control elements for incubating, denaturing, hybridizing, and elongating a set of recombined non-overlapping gene sequences and gap nucleic acids. The system can also include a detector for detecting a nucleic acid produced by elongation of the set of recombined non-overlapping gene sequences and gap nucleic acids, or an encoded product thereof.

DEFINITIONS

Unless otherwise indicated, the following definitions supplement those in the art.

A "set" as used herein refers to a collection of at least two molecule types.

Two nucleic acid sequences "correspond" when they have the same sequence, or when one nucleic acid sequence is a subsequence of the other, or when one sequence is derived, by natural or artificial manipulation from the other.

An "unencrypted RNA" is an RNA generated by trans-splicing at least two RNA segments together. An "unencrypted polypeptide" is a polypeptide generated by trans-splicing at least two polypeptide segments together. The term "polypeptide" includes inteins, exteins, polypeptides, proteins, polyproteins, and the like.

Traits are encrypted using "split gene sequences." Split gene sequences are subsequences of a genetic element. The subsequences can be distributed, e.g., between two parental organisms, but collectively they correspond to the entire genetic element. A "subsequence" of a genetic element is any polynucleotide sequence that is identical or substantially identical to a portion of that genetic element. A "genetic element" includes a segment of DNA involved in producing a polypeptide chain and/or RNA chain. It can include regions preceding (e.g., leader) and following (e.g., trailer) the coding region in addition to intervening sequences (e.g., introns) between individual coding segments (e.g., exons). Genetic elements can include individual exons, introns, promoters, enhancers, genes, gene clusters, gene families, operons, and the like. An "engineered genetic element" is a designed or otherwise artificially constructed genetic element.

An "enhancer-linked split gene sequence" is a subsequence of a genetic element that is linked to an enhancer. An "enhancer" is a cis-acting regulatory nucleotide sequence involved in the transcriptional activation of certain genetic elements. Activation of an enhancer can elevate the rate of transcription. Studies have shown that enhancers can operate when located either 5' or 3' to the transcriptional start site or promoter. They have also been shown to function at distances greater than three kilobases from the start site. Enhancers generally operate as binding sites for transcriptional activating proteins and are tissue specific. They can be incorporated into various expression vectors to optimize the expression of a chosen DNA sequence.

A "trans-acting transcription factor" is a regulatory protein that controls transcription by binding to a specific enhancer, e.g., an enhancer that is linked to an enhancer-linked split gene sequence. The DNA sequence that encodes the transcription factor is not linked to the enhancer sequence upon which that transcription factor acts.

The term "trans-splicing" includes the joining of at least two distinct RNA molecules or of at least two distinct polypeptide molecules to produce at least one trait encrypted RNA or at least one trait encrypted polypeptide, respectively.

A "full-length protein" is a protein with substantially the same sequence domains as a corresponding protein encoded by a natural gene. Such a protein can have altered sequences relative to the corresponding naturally encoded gene, e.g., due to recombination and selection, but unless specified to the contrary, is typically at least about 95% the length of a corresponding naturally encoded protein. The protein can include additional sequences such as purification tags not found in the corresponding naturally encoded protein.

A "toxic genetic element" includes a segment of DNA that encodes a polypeptide, that upon expression, produces sterility in certain organisms, e.g., male sterility in plants. A "toxic polypeptide" is a polypeptide encoded by a toxic genetic element.

The term "non-overlapping gene sequences" refers to polynucleotide sequences that can be homologous to subsequences of a genetic element, but which do not share sequence identity or complementarity amongst themselves. A "gap nucleic acid" is a nucleic acid sequence that includes regions that are identical or complementary to at least two non-overlapping gene sequences.

BRIEF DESCRIPTION OF THE DRAWING

FIG. 1 is a schematic of the use of split genes in encoding traits in F1 but not parentals and only in $1/4^{th}$ of F2.

FIG. 2 is a schematic of a strategy for encrypting engineered traits in F1 using multiple levels of encryption to provide mature gene products.

FIG. 3 is a schematic illustrating the use of split herbicide resistance genes.

FIG. 4 schematically shows a strategy for using split gene sequences for the production of hybrids.

FIG. 5 schematically shows a trans-spliced protein product of the *E. Coli* DnaE gene.

FIG. 6 provides intein sequence information from various organisms.

FIG. 7 illustrates a strategy for the recombination of non-overlapping gene sequences in which no parental genes are rescued.

FIG. 8 shows data involving the recombination of cry3Bb non-overlapping gene sequences with cry1Ba, 1Ca, and 1Ia gene sequences.

DETAILED DISCUSSION OF THE INVENTION

In certain situations it is desirable to provide genes in formats where the final protein to be selected for activity is expressed as an active protein in vitro or in vivo only under controlled conditions. For example, this approach can be useful in cases where a mature protein is toxic to the cell (e.g., RNAses, DNAses, toxins such as ricin, proteases, apoptopsis inducing factors, etc.) and it is therefore advantageous to express the protein in an inactive form, e.g., from split gene sequences, such that it can be conditionally activated. This strategy allows one to direct the expression of otherwise toxic proteins, among many others, and to manipulate genes in ways that have advantages with respect to intellectual property considerations.

The present invention relates to methods of unencrypting trait encrypted gene sequences to provide unencrypted RNAs or polypeptides. The methods of encrypting traits include splitting gene sequences that are subsequently unencrypted by trans-splicing either split RNAs or split polypeptides upon expression of those split gene sequences. The invention also includes methods of providing multiple levels of trait encryption and reliable methods of producing hybrid organisms. Additional methods include those directed at unencrypting engineered genetic elements to provide polypeptide functions and those related to recombining non-overlapping gene sequences. Furthermore, the present invention includes integrated systems and various compositions related to the methods disclosed herein.

In overview, the present invention entails various embodiments of the methods of providing unencrypted RNAs or polypeptides including splitting gene sequences between two parental organisms. Upon mating the two parental organisms, the split gene sequences are expressed and the resulting expression products can then be trans-spliced together at either the RNA or polypeptide levels to provide, e.g., mature mRNAs, or full-length proteins. Trait encrypted RNAs or polypeptides can similarly be provided by splitting gene sequences between a host organism and a vector. Any genetic element can be so encrypted, including certain toxic genetic elements which can provide, e.g., plant breeders with assorted commercial advantages when creating hybrid plants. Multiple levels of encryption can be achieved through the use of enhancer-linked split gene sequences.

The methods of unencrypting genetic elements to provide polypeptide function can involve splitting functionally related genetic elements between two parental organisms or between a host organism and a vector. Functional protein products of the genetic elements are created, e.g., upon mating or infection. Furthermore, the invention provides methods of recombining non-overlapping gene sequences that would not otherwise recombine. This method includes using gap nucleic acid sequences that overlap, e.g., share regions of complementarity with two or more of the non-overlapping gene sequences.

The following provides details regarding various aspects of the methods of providing unencrypted RNAs or polypeptides, including sequence selection, synthesis and encryption. It also provides details pertaining to the methods of evolving engineered proteins and recombining non-overlapping nucleic acid sequences, to applicable integrated systems, and to various nucleic acid compositions.

Unencrypting Trait Encrypted Gene Sequences to Provide Unencrypted RNAS or Polypeptides The methods of the present invention include those related to unencrypting gene sequences, e.g., DNA or cDNAs, to provide unencrypted RNAs or polypeptides. The methods include providing split gene sequences in which each split gene sequence includes, e.g., a subsequence of a gene, and transcribing those split gene sequences to provide a population of RNA segments. This process optionally occurs in vitro or in vivo. At least two of those RNA segments can be trans-spliced together (discussed further, infra) to provide an unencrypted RNA. The unencrypted RNA is optionally selected for a desired trait or property, or translated to provide an unencrypted polypeptide, e.g., a full-length protein, which can also optionally be selected for a desired trait or property.

Alternatively, the population of RNA segments can be translated to provide a population of polypeptide segments and two or more of those polypeptides can be trans-spliced together (discussed further, infra) to provide an unencrypted polypeptide that is optionally selected for a desired trait or property.

In one embodiment of these methods, two parental organisms, each of which includes a plurality of split gene sequences (introduction of split gene sequences is described, infra) can be mated to produce a progeny organism that includes split gene sequences from both parents. Thereafter, those split gene sequences can be transcribed to provide a population of RNA segments, which as above are optionally trans-spliced together to provide unencrypted RNAs or the RNA segments are optionally translated to provide a population of polypeptides which can then be trans-spliced together to provide unencrypted polypeptides.

FIG. 1 illustrates the commercial advantages of splitting, e.g., the *Bacillus thuringiensis* (Bt) toxin gene between two plant parentals. Neither parent would express the complete Bt toxin gene, because the amino-terminal portion of the gene is present only in first parent 100, while the carboxyl-terminal portion of the gene is only present in second parent 102. A cross between these two parents produces F1 seeds in which both portions of the gene are present. For example, the F1 seeds are then typically sold to consumers, because the F1 plants would express mature trans-spliced Bt toxin which affords protection from insect attack without the need for spraying. However, F2 seeds would be of little use to consumers as only 25 percent of those seeds would contain both portions of the split Bt toxin gene. This logic is applicable to any gene of interest.

Selection of Parental Organisms

As described below, essentially any plant can be transduced with the nucleic acid sequences taught herein. Some suitable plants for use with respect to the methods of the present invention, include those selected from the genera: Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Heterocallis, Nemesia, Pelargonium, Panicum, Pennisetum, Ranunculus, Senecio, Salpiglossis, Cucumis, Browaalia, Lolium, Malus, Apium, Gossypium, Vicia, Lathyrus, Lupinus, Pachyrhizus, Wisteria, and Stizolobium.

Important commercial crops include both monocots and dicots. Monocots include plants in the grass family plants (Gramineae), such as plants in the sub-families Fetucoideae and Poacoideae, which together include several hundred genera including plants in the genera Agrostis, Phleum, Dactylis, Sorghum, Setaria, Zea (e.g., corn), Oryza (e.g., rice), Triticum (e.g., wheat), Secale (e.g., rye), Avena (e.g., oats), Hordeum (e.g., barley), Saccharum, Poa, Festuca, Stenotaphrum, Cynodon, Coix, Olyreae, Phareae, Glycine, Pisum, Cicer, Phaseolus, Lens, Arachis, and many others. Additional commercially important crop plants are, e.g., from the families Compositae (the largest family of vascular plants, including at least 1,000 genera, including important commercial crops such as sunflower), and Leguminosae or "pea family," which includes several hundred genera, including many commercially valuable crops such as pea, beans, lentil, peanut, yam bean, cowpeas, velvet beans, soybean, clover, alfalfa, lupine, vetch, sweet clover, wisteria, and sweetpea. Other common crops applicable to the methods of the invention, include rapeseed and canola.

In addition to plants, microbes, fungi, and animals can be transduced with the target nucleic acid sequences of the invention. Various methods have been developed, especially for use in animal cells, to facilitate this process, including the use of polycations such as DEAE-dextran (McCutchan, J. H. and Pagano, J. S. (1968) *J. Natl. Cancer Inst.* 41, 351–357 and Kawai, S. and Nishizawa, M. (1984) *Mol. Cell. Biol.* 4, 1172–1174), calcium phosphate coprecipitation (Graham, F. L. and Van der Eb, A. J. (1973) *Virology* 52, 456–467), electroporation (Neuman, E. et al. (1982) *EMBO J.* 7, 841–845), lipofection (Felgner, P. L. et al. (1987) *Proc. Natl. Acad. Sci. USA* 84, 7413–7417), retrovirus vectors (Cepko, C. L. et al. (1984) *Cell* 37, 1053–1062), and microinjection (Capecchi, M. R. (1980) *Cell* 22, 479–488).

In addition to the references noted throughout, one of skill can find guidance as to animal cell culture in Freshney, *Culture of Animal Cells, a Manual of Basic Technique*, 3$^{rd}$ Ed., Wiley-Liss, New York (1994) and the references cited therein provides a general guide to the culture of cells. See also, Kuchler, et al. (1977) *Biochemical Methods in Cell Culture and Virology*, Kuchler, R. J., Dowden, Hutchinson and Ross, Inc., and Inaba, et al. (1992) *J. Exp. Med.*, 176:1693–1702. Additional information on cell culture is found in *Current Protocols in Molecular Biology*, F. M. Ausubel et al., eds., Current Protocols, a joint venture between Greene Publishing Associates, Inc. and John Wiley & Sons, Inc., (supplemented through 1999) (Ausubel), Sambrook et al., *Molecular Cloning—A Laboratory Manual* (2nd Ed.), Vol. 1–3, Cold Spring Harbor Laboratory, Cold Spring Harbor, N.Y., 1989 (Sambrook), and Berger and Kimmel, *Guide to Molecular Cloning Techniques, Methods in Enzymology* volume 152 Academic Press, Inc., San Diego, Calif. (Berger). Cell culture media are described in Atlas and Parks (eds) *The Handbook of Microbiological Media* (1993) CRC Press, Boca Raton, Fla. Generally, one of skill is fully able to transduce cells from animals, plants, fungi, bacteria and other cells using available techniques. Moreover, one of skill can transduce whole organisms with the nucleic acids of the present invention using available techniques.

Vector-Mediated Trait Encryption

The concept of splitting genes to encrypt traits disclosed, supra, can be generalized to include the delivery of split gene sequence using a vector, e.g., a viral vector. This strategy can be particularly useful, e.g., when it proves difficult to provide engineered organisms with sufficiently tight regulation to prevent a highly toxic protein from being expressed.

In one embodiment of the present invention, a host organism (e.g., one of the types of parental organisms discussed, supra) that includes a plurality of split gene sequences is infected with a vector, such as a virus, that also includes a plurality of split gene sequences to produce an infected organism that includes both host and vector split gene sequences. As with the other embodiments of these methods, the split gene sequences can be transcribed to provide a population of RNA segments which, in turn, can be trans-spliced together and then translated, or translated directly and trans-spliced as polypeptide segments to provide desired unencrypted proteins.

In certain preferred embodiments of these vector-mediated methods, the vectors are plant viruses. Plant viruses designed to have new and desirable transformation and expression properties are also preferred embodiments. Viruses are typically useful as vectors for expressing exogenous DNA sequences, e.g., split gene sequences, in a transient manner in plant hosts. In contrast to Agrobacterium-mediated transformation, discussed infra, which results in the stable integration of DNA sequences in the plant genome, viral vectors are generally replicated and expressed without the need for chromosomal integration. Plant virus vectors offer a number of advantages, including as follows:

(1) DNA copies of viral genomes can be readily manipulated in *E. coli*, and transcribed in vitro, to produce infectious RNA copies;

(2) Naked DNA, RNA, or viral particles can be easily introduced into mechanically wounded leaves of intact plants;

(3) High copy numbers of viral genomes per cell results in high expression levels of introduced genes;

(4) Common laboratory plant species as well as monocot and dicot crop species are readily infected by various virus strains;

(5) Infection of whole plants permits repeated tissue sampling of single library clones;

(6) Recovery and purification of recombinant viral particles is simple and rapid; and, (7) As replication occurs without chromosomal insertion, expression is not subject to positional effects.

Over 650 plant viruses have been identified, and are amenable in the vector-mediated methods of the invention. Plant viruses are known which infect every major food-crop, as well as most species of horticultural interest. The host range varies between viruses, with some viruses infecting a broad host range (e.g., alfalfa mosaic virus infects more than 400 species in 50 plant families) while others have a narrow host range, sometimes limited to a single species (e.g., barley yellow mosaic virus). Host range is among the many traits for which it is possible to select appropriate vectors according to the methods provided by the present invention.

Approximately 75% of the known plant viruses have genomes which are single-stranded (ss) messenger sense (+) RNA polynucleotides. Major taxonomic classifications of ss-RNA(+) plant viruses include the bromovirus, capillovirus, carlavirus, carmovirus, closterovirus, comovirus, cucumovirus, fabavirus, furovirus, hordeivirus, ilarvirus, luteovirus, potexvirus, potyvirus, tobamovirus, tobravirus, tombusvirus, and many others. Other plant viruses exist which have single-stranded antisense (−) RNA (e.g., rhabdoviridae), double-stranded (ds) RNA (e.g., cryptovirus, reoviridae), or ss or ds DNA genomes (e.g., geminivirus and caulimovirus, respectively).

Preferred embodiments of the invention include engineered vectors that are both RNA and DNA viruses. Examples of such embodiments include viruses selected from among: an alfamovirus, a bromovirus, a capillovirus, a carlavirus, a carmovirus, a caulimovirus, a closterovirus, a comovirus, a cryptovirus, a cucumovirus, a dianthovirus, a fabavirus, a fijivirus, a furovirus, a geminivirus, a hordeivirus, a ilarvirus, a luteovirus, a machlovirus, a maize chlorotic dwarf virus, a marafivirus, a necrovirus, a nepovirus, a parsnip yellow fleck virus, a pea enation mosaic virus, a potexvirus, a potyvirus, a reovirus, a rhabdovirus, a sobemovirus, a tenuivirus, a tobamovirus, a tobravirus, a tomato spotted wilt virus, a tombusvirus, and a tymovirus.

Plant viruses can be engineered as vectors to accomplish a variety of functions. Examples of both DNA and RNA viruses have been used as vectors for gene replacement, gene insertion, epitope presentation and complementation, (see, e.g., Scholthof, et al. (1996) "Plant Virus Gene Vectors for Transient Expression of Foreign Proteins in Plants," *Annu. Rev. Phytopathol.* 34:299–323.)

Methods for the transformation of plants and plant cells using sequences derived from plant viruses include direct transformation techniques relating to DNA molecules, see e.g., Jones, ed. (1995) *Plant Gene Transfer and Expression Protocols*, Humana Press, Totowa, N.J., for a recent compilation. In addition viral sequences can be cloned adjacent T-DNA border sequences and introduced via Agrobacterium-mediated transformation, or Agroinfection. Viral particles comprising the plant virus vectors of the invention can also be introduced by mechanical inoculation using techniques well known in the art (see e.g., Cunningham and Porter, eds. (1997) *Methods in Biotechnology, Vol.3. Recombinant Proteins from Plants: Production and Isolation of Clinically Useful Compounds*, for detailed protocols). Briefly, for experimental purposes, young plant leaves are dusted with silicon carbide (carborundum), then inoculated with a solution of viral transcript, or encapsidated virus and gently rubbed. Large scale adaptations for infecting crop plants are also well known in the art, and typically involve mechanical maceration of leaves using a mower or other mechanical implement, followed by localized spraying of viral suspensions, or spraying leaves with a buffered virus/carborundum suspension at high pressure. Any of these techniques, mentioned above, can be adapted to the vector-mediated trait encryption methods of the present invention.

Enhancer-Linked Split Gene Sequences and Trans-Acting Factors

In another embodiment of these methods, a first parental organism can include a plurality of first enhancer-linked split gene sequences, each of which includes a subsequence of a genetic element, e.g., a herbicide resistance gene, with a first enhancer sequence linked thereto. As depicted in FIG. 2, this first parental organism also includes first trans-acting transcription factor sequences (TAF 1) that are unlinked to the plurality of first enhancer-linked split gene sequences. See also, FIG. 3. This embodiment also includes a second parental organism that includes a second plurality of enhancer-linked split gene sequences in which, similarly, each enhancer-linked split gene sequence includes a subsequence of the genetic element with a second enhancer sequence linked thereto. (FIG. 2). The second parental organism also includes second trans-acting transcription factor sequences (TAF 2) that are unlinked to the second plurality of enhancer-linked split gene sequences.

In this embodiment, the two parental organisms can be mated to produce a progeny organism that includes the first and the second plurality of enhancer-linked split gene sequences and the first and the second trans-acting transcription factor sequences. (FIG. 2). The first and the second plurality of enhancer-linked split gene sequences can be transcribed to provide a plurality of RNA segments in which the first plurality of enhancer-linked split gene sequences are regulated by TAF 2 and the second plurality of enhancer-linked split gene sequences are regulated by TAF 1. The plurality of RNA segments are optionally trans-spliced directly and then translated or translated directly and then trans-spliced together as polypeptides to provide trait encrypted polypeptides.

Figure 3:
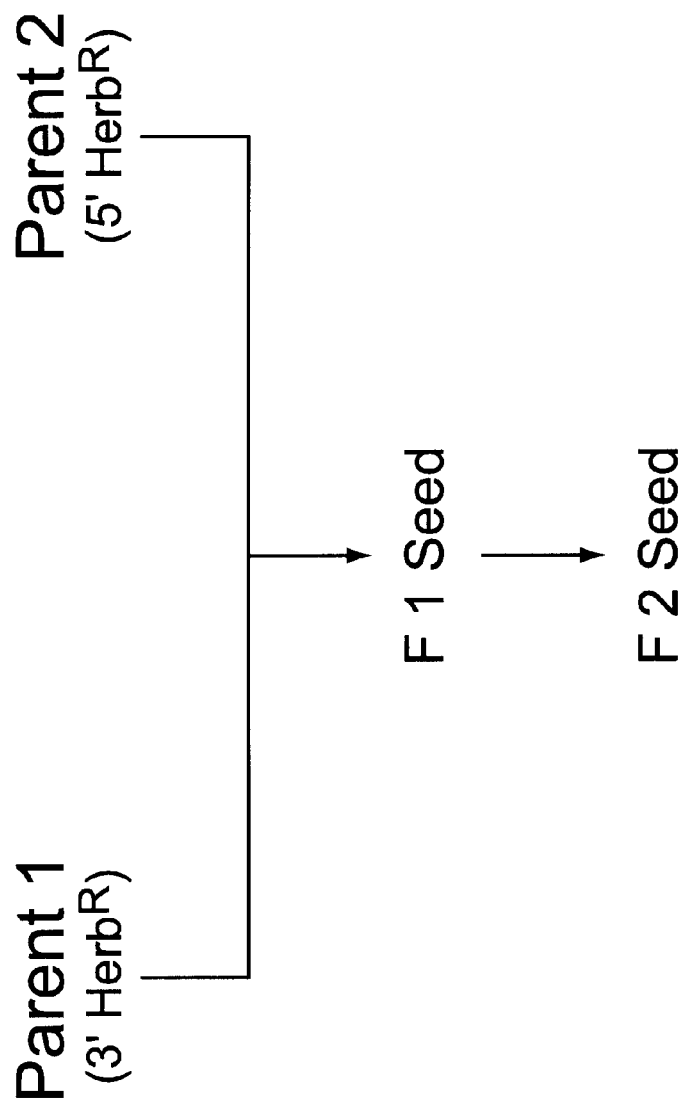

As shown in FIG. 3, F1 seeds produced using this embodiment of the present invention could be sold to consumers as the complete herbicide resistance gene product would be expressed in plants produced therefrom. However, F2 seeds would not be useful, because only $\frac{1}{16}^{th}$ of those seeds would have all four components, i.e., the 5' and 3'-portions of the split herbicide resistance gene in addition to both TAF 1 and 2.

Enhancers are sequences involved in stimulating transcription initiation. They can be located at substantial distances from the startpoints of coding sequences, either on the 5' or the 3' side of them, and in either orientation. They can include various modular components that resemble those of the promoter, but those components are generally organized in a closely packed sequence. Enhancer sequences are targets for tissue-specific or temporal regulation and can increase the activity of any promoter located in their vicinity.

Transcription factors, like the trans-acting transcription factors of the present invention, are proteins that are needed for the initiation of transcription. They are distinct from RNA polymerases. They can act by recognizing and binding to cis-acting sites, i.e., the enhancers linked to split gene sequences. Transcription factors can also recognize other factors or RNA polymerases, or can be incorporated into an initiation complex only in the presence of several other proteins. There are many references that can be consulted regarding various aspects of enhancers, transcription factors, and their interaction, e.g., Banjeri, J. et al. (1981) "Expression of β-globin gene is enhanced by remote SV40," *Cell* 27, 299–308; Zenke, M. et al. (1986) "Multiple Motifs are Involved in SV40 Enhancer Function," *EMBO J.* 5, 387–397; Mueler-Storm, H. P. et al. (1989) "An enhancer stimulates transcription in trans when attached to the promoter via a protein bridge," *Cell* 58, 767–777; Kustu, A. K. and Weiss, D. S. (1991) "Prokaryotic Transcriptional Enhancers and Enhancer-Binding Proteins," *Trends Biochem. Sci.* 16:397–402; Kadonaga, J. et al. (1987) "Isolation of cDNA Encoding Transcription Factor Sp1 and functional analysis of the DNA Binding Domain," *Cell* 51. 1079–1090; Ma, J. and Ptashne, M. (1987) "A new class of Yeast Transcriptional Activators," *Cell* 79, 93–105; and Muller, M. M. et al. (1988) "Enhancer Sequences and the Regulation of Gene Transcription," *Eur. J. Biochem.* 176, 485–495.

Toxic Genetic Elements

It is not uncommon for hybrid offspring to outperform their parents by various measures, including yield, adaptability to environmental changes, disease resistance, pest resistance, solids content, sugar content, water content, and the like. As such, there is considerable commercial importance in generating hybrids with desirable traits. The improved properties observed in hybrids relative to parents are collectively referred to as "hybrid vigor" or "heterosis." Hybridization between parents of dissimilar genetic stock has been used in animal husbandry and especially for improving major plant crops, such as corn, sugarbeet and sunflower.

It has proven difficult, however, to commercialize genetically engineered variants of many plants due to the fact that hybrids cannot be bred reliably. In the case of corn, for example, hybrids have been created by the laborious task of removing the tassels from one parent and pollinating with another. In general, one attempt to address the problems related to hybrids has been to engineer plants that conditionally express toxins, specifically in pollen, that render plants sterile with respect to self-pollination. However, this approach has raised the concern of regulators, e.g., due to the risk of sterility genes spreading to wild plants. Furthermore, this technique requires engineering an expression system that is tightly regulated to prevent expression of the toxic genes in the soma of these plants. As discussed throughout this disclosure, the methods of encrypting traits provided by the present invention resolve many of these issues.

For example, the present invention provides a solution to the problems associated with the production of hybrids by encoding engineered genes, e.g., Bt toxin genes (FIG. 1), in split gene sequences. In doing so, the desired protein product is then expressed upon breeding plants that encode, e.g., each half of the split gene sequence. A full-length protein is made by either trans-splicing mRNA fragments corresponding to the split gene sequences followed by translation, or as depicted in FIG. 1, translating the mRNA fragments directly and then trans-splicing at the polypeptide level. This solution provides plants breeders with potential commercial benefits, as consumers would not be able to easily propagate seed that breeds true, i.e., that are homozygous for the trait under consideration (see e.g., FIG. 4), but without the costs otherwise associated with the creation of plants engineered for male sterility.

Figure 4:
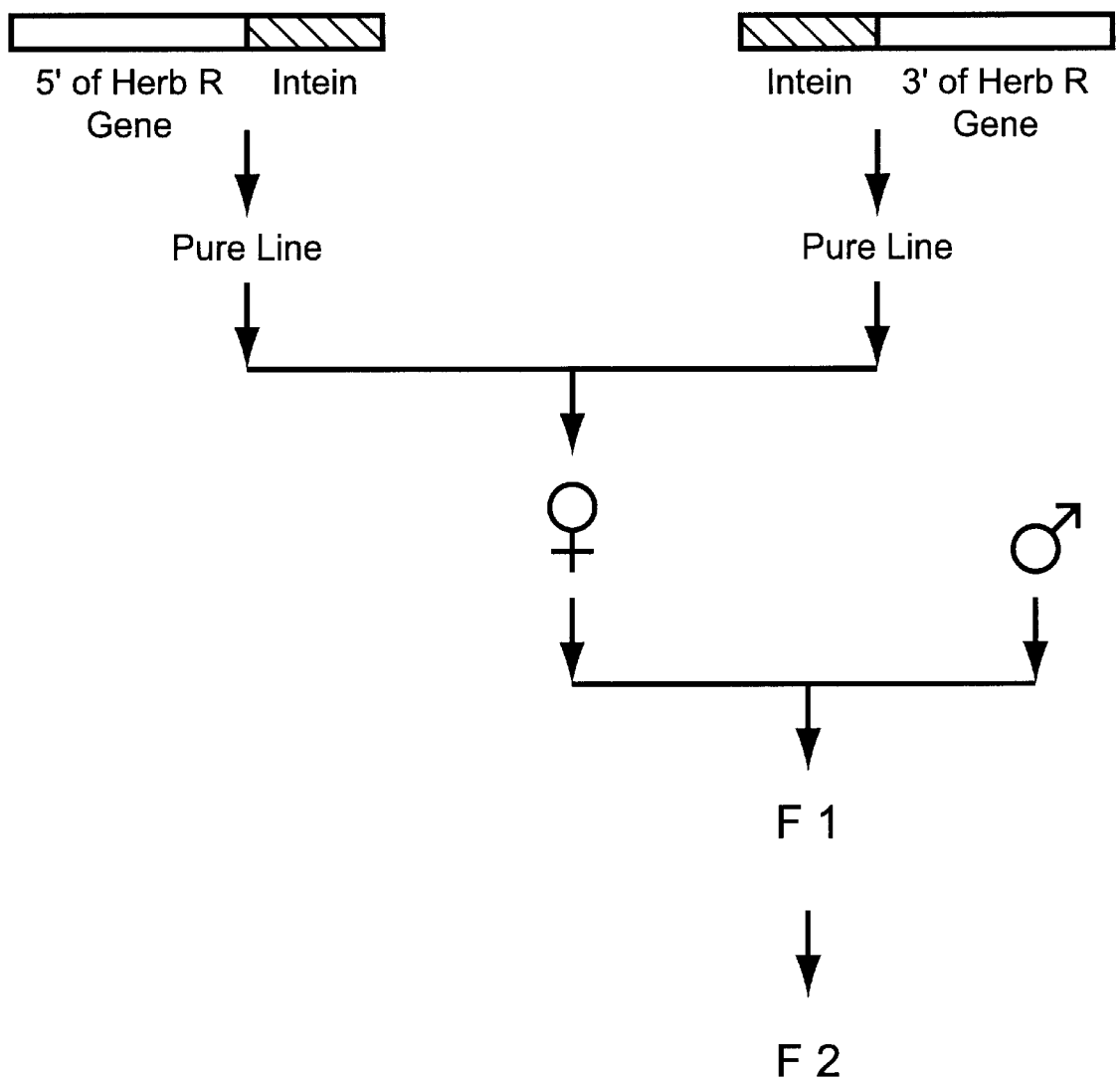

As depicted in FIG. 4, in another embodiment of the present invention, two parental organisms, each including split gene sequences in which each split gene sequence includes a subsequence of a toxic genetic element are mated and the split gene sequences can be expressed in the progeny organism to provide a toxic polypeptide after trans-splicing at the RNA or the polypeptide levels as described above. The toxic polypeptide, in turn, renders the progeny organism incapable of reproducing when it is male, i.e., the progeny organism acquires a "hybrid vigor." (FIG. 4). However, the progeny organism can reproduce when it is female and when it does, the progeny organism produces hybrid progeny organisms in which the toxic genetic element is not expressed. In a related embodiment of this method, a toxic polypeptide renders the progeny organism incapable of reproducing when it is female. However, this progeny organism is capable of reproducing when it is male and when it does, the progeny organism produces hybrid progeny organisms in which the toxic genetic element is not expressed.

As further depicted in FIG. 4, F1 plants would not express the toxic gene product and as such, there would be no loss of yield. However, F2 may not be useful, because the "hybrid vigor" of F1 is lost.

Trans-Splicing RNAs and Polypeptides

Trans-splicing includes splicing two independently transcribed pre-mRNAs together. The mechanism of trans-splicing proceeds through two phosphoryl transfer reactions similar to that of cis-splicing. Moore, J. M. et al. In *The RNA World* (eds Gesteland, R. F. & Atkins, J. F.) 303–357 (Cold Spring Harbor Laboratory Press, New York, 1993). The first yields the formation of a 2'-5' phospodiester bond producing a Y-shaped branched intermediate, equivalent to the lariat intermediate in cis-splicing. Id. The second reaction, exon ligation, also proceeds as in cis-splicing. Additionally, sequences at the 3' splice site and some of the small nuclear ribonucleoprotein particles (snRNPs) that catalyze the trans-splicing reaction closely resemble their counterparts involved in cis-splicing. Murphy, W. J. et al. (1986) "Identification of a Novel Branch Structure as an Intermediate in Trypanosome MRNA Processing: Evidence for Trans-Splicing," *Cell* 47, 517–525 and Curotto de Lafaille, M. A. (1992) "Gene Expression in Leishmania: Analysis of Essential 5' DNA Sequences," *Proc. Natl. Acad. Sci. USA* 89, 2703–2707. As applicable to the present invention, trans-splicing of RNAs can also involve a process in which an intron of one pre-mRNA interacts with an intron of a second pre-mRNA, enhancing the recombination of splice sites between two conventional pre-mRNAs. Puttaraju, M. et al. (1999) "Spliceosome-Mediated RNA Trans-Splicing as a Tool for Gene Therapy," *Nat. Biotechnol.* 17, 246–252. This type of trans-splicing was demonstrated, e.g., in c-myb pre-mRNA (Vellard, M. et al. (1992) "A Potential Splicing Factor is Encoded by Opposite Strand of the Trans-Spliced c-myb Exon," *Proc. Natl. Acad. Sci. USA* 89, 2511–2515) and with respect to SV40 transcripts in cultured cells (Eul, J. et al. (1995) "Experimental Evidence for RNA Trans-Splicing in Mammalian Cells," *EMBO J.* 14, 3226–3235). Relatively efficient trans-splicing in vitro has been shown between RNAs capable of base pairing to each other. Konarsha, M. M. et al. (1985) "Trans-Splicing of mRNA Precursors In Vitro," *Cell* 42, 165–171 and Pasman, Z. and Garcia-Blanco, M. A. (1996) "The 5' and 3' Splice Sites Come Together Via A Three-Dimensional Diffusion Mechanism," *Nucleic Acids Res.* 24, 1638–1645. For purposes of the present invention, the use of spliceosome-mediated targeted trans-splicing reactions to generate trans-spliced chimeric mRNA and functional chimeric proteins therefrom has been confirmed both in vitro and in vivo. Puttaraju, M. et al. (1999) *Nat. Biotechnol.* 17, 246–252, supra. As such, this mechanism can be used in the various embodiments of the present invention to provide trait encrypted RNAs.

Figure 5:
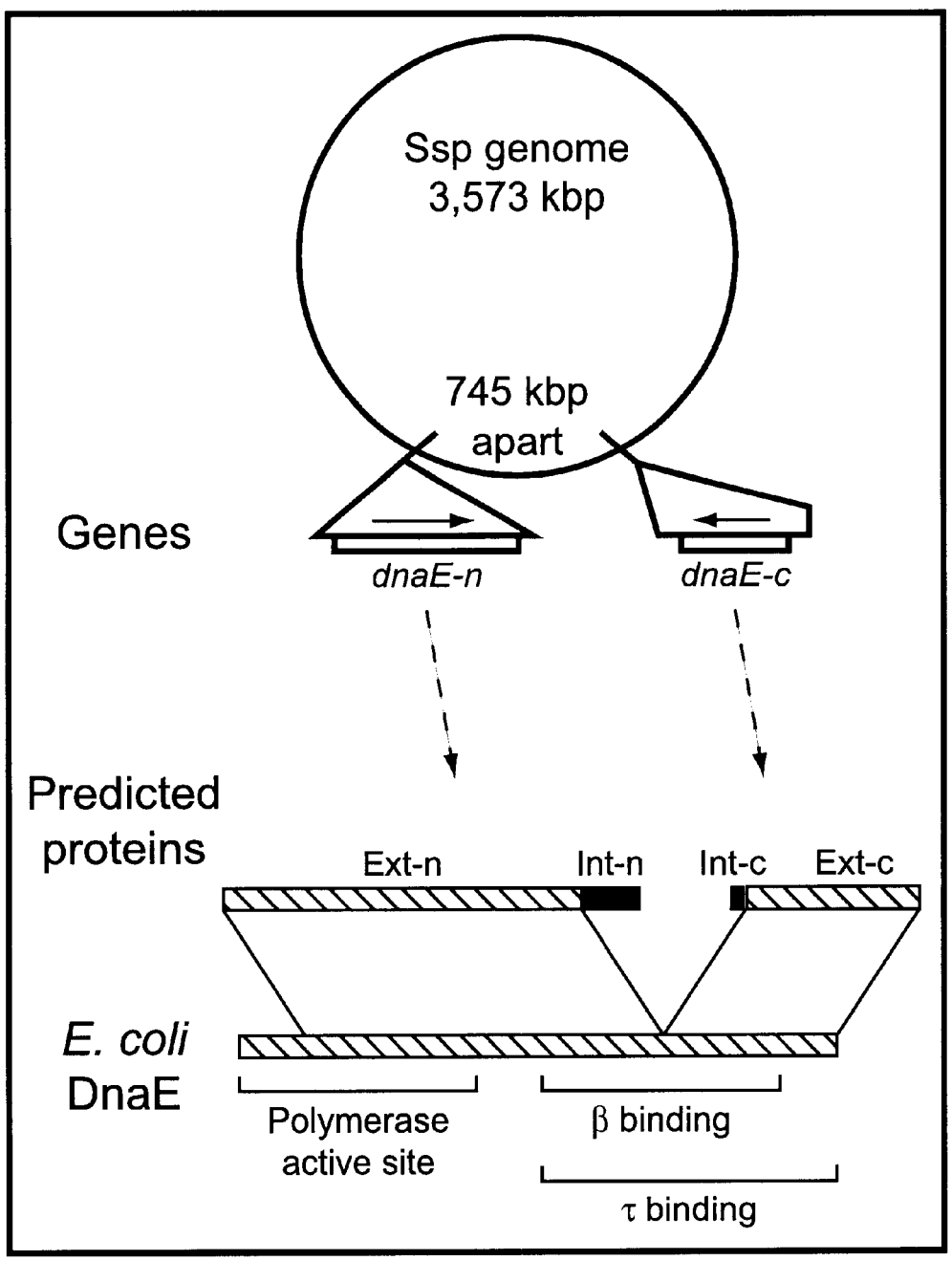

In addition to trans-splicing of RNAs, trans-splicing of inteins is also used in the present invention. In one preferred embodiment, proteins of interest are encoded in split genes which are expressed to produce polypeptide fragments. These fragments are subsequently recombined to form the protein of interest. Examples of trans-intein splicing systems are available, such as the DnaE gene, encoded by dnaE-n and dnae-c in the Synchocystis sp. PCC6803 genome. This is illustrated in FIG. 5, where DnaE-related sequences are denoted as exteins Ext-n and Ext-c, while intein-related sequences are indicated as Int-n and Int-c. Furthermore, the functional domains of the trans-spliced protein product are also shown. FIG. 6 provides DnaB and DnaE intein sequence information from various organisms, including *Porphyra purpurea, Rhodothermus marinus*, and *Mycobacterium tuberuclosis*.

Unencrypting Engineered Genetic Elements to Provide Polypeptide Function

Trait encryption can also be accomplished utilizing post-translational modifications. For example, there are proteins that ligate biotin onto surface lysines in a site-specific manner. One can take advantage of this and other equivalent mechanisms (e.g., glycosylation, proteolysis, farnesylation, cholesterol esterification, acetylation, methylation, phosphorylation, dephosphorylation, and the like) for purposes of encryption by evolving a variant of a protein that requires biotinylation (or any other modification) for activity. Methods of evolving proteins, including non-overlapping gene sequence mediated-recombination, among many others, are discussed further, infra. A biotin ligase can be evolved that activates another protein by specifically ligating biotin onto the other protein in vivo. This provides an additional encryption system where, for instance, transgenic wheat plants require both the biotin ligase and an engineered glyphosate resistance gene to be present in the same plant in order to get functional protein. One commercial advantage of these methods is that the producer of the seed with the engineered trait then controls the ability to produce a seed that breeds true.

The methods of unencrypting engineered genetic elements to provide encrypted polypeptide functions of the present invention can occur in vitro or in vivo. The methods include providing a first engineered genetic element that corresponds to an encoded first polypeptide, e.g., an engineered biotin ligase that is functional. It also includes providing a second engineered genetic element that corresponds to an encoded second polypeptide, e.g., an engineered biotin dependent glyphosate resistance polypeptide, that is nonfunctional in the absence of the post-translational modification, i.e., biotinylation performed by the first polypeptide. Thereafter, the first and second engineered genetic elements can be mixed and expressed to produce the encoded first and second polypeptides. The encoded first polypeptide then modifies the encoded second polypeptide to provide a functional encoded second polypeptide.

Embodiments of these methods that can be performed in vivo include mating a first parental organism that includes the first engineered genetic element and a second parental organism that includes the second engineered genetic element to produce a progeny organism that includes both engineered genetic elements. Thereafter, the genetic elements in the progeny organism can be expressed to produce the encoded first and second polypeptides. The first and second parental organisms of this embodiment can be, e.g., animals, plants, fungi, or bacteria. The selection of suitable parental organisms is discussed further, supra. However, in certain preferred embodiments they are plants or yeast.

Another embodiment of these methods of unencrypting engineered genetic elements that can be performed in vivo includes infecting a host organism that includes a first engineered genetic element with a vector that includes a second engineered genetic element to produce an infected organism. Following infection, the infected organism includes both the first and the second engineered genetic elements. Thereafter, both engineered genetic elements can similarly be expressed in the progeny organism to produce the encoded first polypeptide which modifies the second polypeptide to render it functional.

Selection of Trait Encrypted RNAS and polypeptides and Engineered Genetic Elements The precise selection technique used in the methods disclosed herein is not a critical aspect of the invention. In general, one of skill can practice appropriate screening or selection methods, by reference to the activity to be selected for. Furthermore, methods of transducing cells, including plant and animal cells, with nucleic acids are generally available, as are methods of expressing proteins encoded by those nucleic acids. These and other methods are described and related references are given, infra.

Non-Overlapping Gene Sequence Recombination

Figure 7:
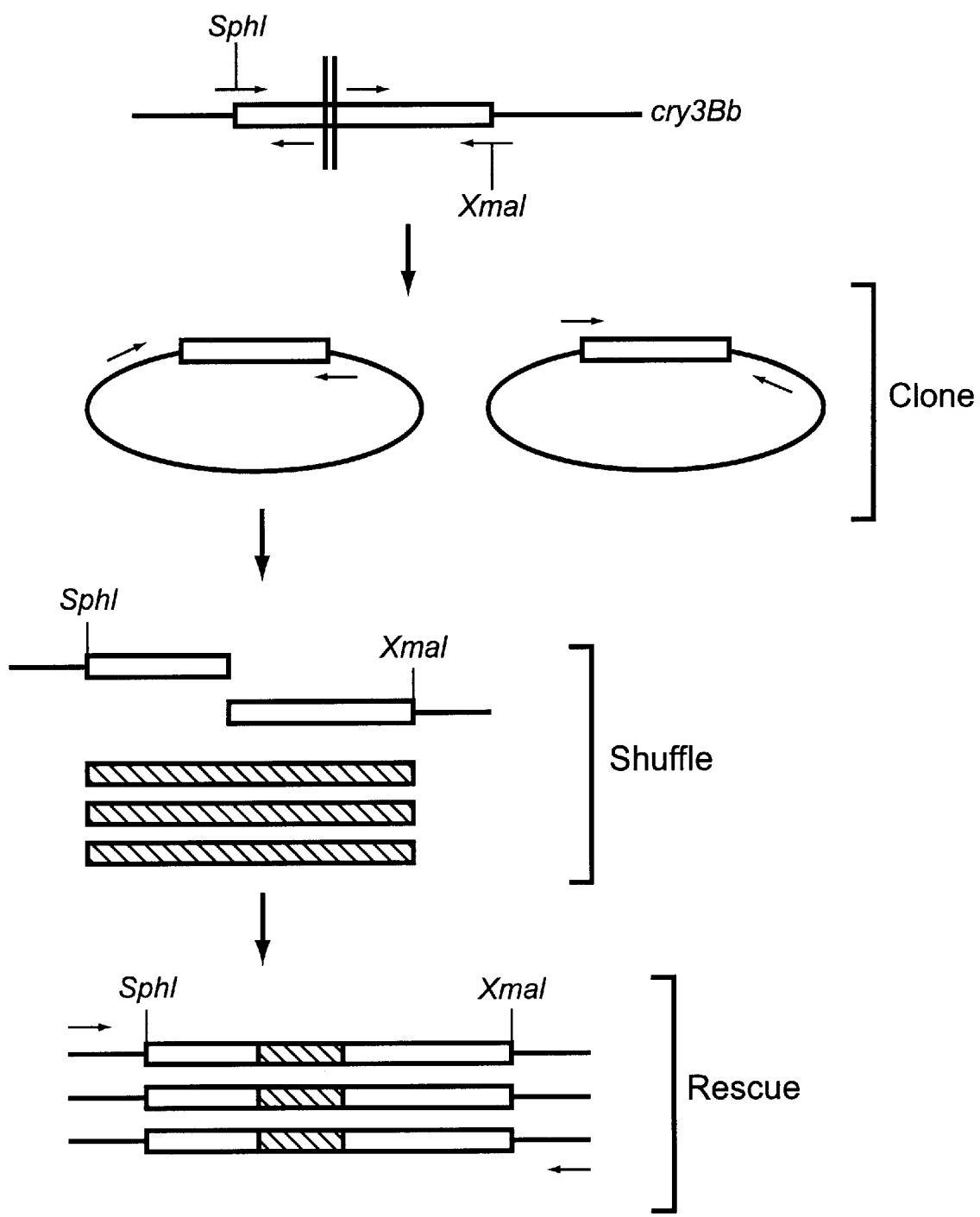

When several homologous genes are recombined, it is possible that the original genes are reassembled and rescued. To avoid simply recovering the original genes, discontinued genes, i.e., non-overlapping gene sequences can be used. Since the gene sequences to be recombined are non-overlapping, they are not rescued unless the non-overlapping sequences are connected with the other genes by recombination. This concept is illustrated in FIG. 7, where two cloned non-overlapping cry3Bb gene sequences are recombined with a population of gap nucleic acids, which are represented by the black sequences in the figure. As shown, no complete parental cry3Bb genes are recovered from the recombination step. (FIG. 7).

The methods of recombining non-overlapping gene sequences of the present invention can occur in vitro or in vivo. The methods include providing a plurality of non-overlapping gene sequences in which each non-overlapping gene sequence corresponds to a different subsequence of a genetic element, e.g., a gene. The methods further include providing a plurality of gap nucleic acid sequences in which each gap nucleic acid sequence overlaps two or more of the non-overlapping gene sequences. The non-overlapping gene sequences can be recombined with the gap nucleic acid sequences to provide recombined non-overlapping gene sequences. As described further below, the recombined non-overlapping gene sequences are optionally selected for a desired trait or property and then recombined again. This process of selecting and recombining the recombined non-overlapping gene sequences can be repeated until a desired recombined genetic element is obtained.

Figure 8:
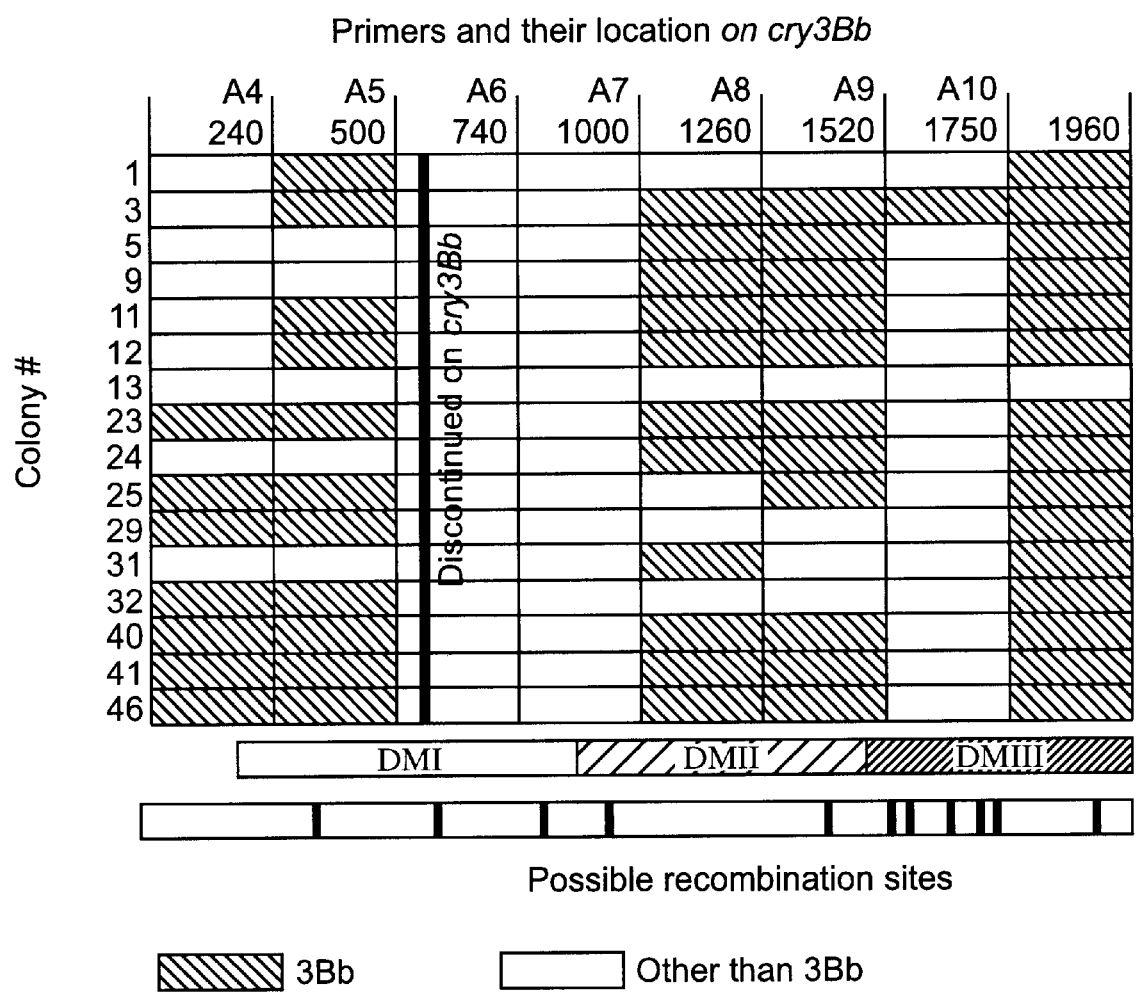

Two non-overlapping gene sequences derived from a cry3Bb gene were recombined and a plurality of gap nucleic acid sequences derived from a cry1Ba, a cry1Ca, and a cry1Ia gene using these methods. The results of this recombination are depicted in FIG. 8. The recombined DNA was recovered with primers specific to the start and end of the cry3Bb gene. Recovered DNA was cloned and 16 colonies were picked for PCR analysis using seven primers (represented by A4 to A10) at various locations within cry3Bb and one at the end of the gene. The boxes, representing approximately 250 nucleotides prior to an annealing site, are darkened to indicate where primers annealed and produced the right-sized PCR fragment. (FIG. 8).

Diversity Generating Strategies

The polynucleotides of the present invention, e.g., the engineered genetic elements discussed, supra, are optionally used as substrates for a variety of recombination reactions and/or mutagenic techniques. In general, the nucleic acids provided by the methods herein can be recombined and/or mutagenized to produce encoded protein products with desired properties. A variety of such reactions are known, including those developed by the inventors and their co-workers.

Descriptions of a variety of diversity generating procedures for generating modified nucleic acid sequences, such as the split gene sequences (e.g., enhancer-linked split gene sequences, etc.), toxic genetic elements, engineered genetic elements, or the like of the invention, are found the following publications and the references cited therein: Stemmer, et al. (1999) "Molecular breeding of viruses for targeting and other clinical properties" *Tumor Targeting* 4:1–4; Ness et al. (1999) "DNA Shuffling of subgenomic sequences of subtilisin" *Nature Biotechnology* 17:893–896; Chang et al. (1999) "Evolution of a cytokine using DNA family shuffling" *Nature Biotechnology* 17:793–797; Minshull and Stemmer (1999) "Protein evolution by molecular breeding" *Current Opinion in Chemical Biology* 3:284–290; Christians et al. (1999) "Directed evolution of thymidine kinase for AZT phosphorylation using DNA family shuffling" *Nature Biotechnology* 17:259–264; Crameri et al. (1998) "DNA shuffling of a family of genes from diverse species accelerates directed evolution" *Nature* 391:288–291; Crameri et al. (1997) "Molecular evolution of an arsenate detoxification pathway by DNA shuffling," *Nature Biotechnology* 15:436–438; Zhang et al. (1997) "Directed evolution of an effective fucosidase from a galactosidase by DNA shuffling and screening" *Proc. Natl. Acad. Sci. USA* 94:4504–4509; Patten et al. (1997) "Applications of DNA Shuffling to Pharmaceuticals and Vaccines" *Current Opinion in Biotechnology* 8:724–733; Crameri et al. (1996) "Construction and evolution of antibody-phage libraries by DNA shuffling" *Nature Medicine* 2:100–103; Crameri et al. (1996)

"Improved green fluorescent protein by molecular evolution using DNA shuffling" *Nature Biotechnology* 14:315–319; Gates et al. (1996) "Affinity selective isolation of ligands from peptide libraries through display on a lac repressor 'headpiece dimer'" *Journal of Molecular Biology* 255:373–386; Stemmer (1996) "Sexual PCR and Assembly PCR" In: *The Encyclopedia of Molecular Biology.* VCH Publishers, New York. pp.447–457; Crameri and Stemmer (1995) "Combinatorial multiple cassette mutagenesis creates all the permutations of mutant and wildtype cassettes" *BioTechniques* 18:194–195; Stemmer et al., (1995) "Single-step assembly of a gene and entire plasmid form large numbers of oligodeoxy-ribonucleotides" *Gene,* 164:49–53; Stemmer (1995) "The Evolution of Molecular Computation" *Science* 270: 1510; Stemmer (1995) "Searching Sequence Space" *Bio/Technology* 13:549–553; Stemmer (1994) "Rapid evolution of a protein in vitro by DNA shuffling" *Nature* 370:389–391; and Stemmer (1994) "DNA shuffling by random fragmentation and reassembly: In vitro recombination for molecular evolution." *Proc. Natl. Acad. Sci. USA* 91:10747–10751.

Mutational methods of generating diversity include, for example, site-directed mutagenesis (Ling et al. (1997) "Approaches to DNA mutagenesis: an overview" *Anal Biochem.* 254(2): 157–178; Dale et al. (1996) "Oligonucleotide-directed random mutagenesis using the phosphorothioate method" *Methods Mol. Biol.* 57:369–374; Smith (1985) "In vitro mutagenesis" *Ann. Rev. Genet.* 19:423–462; Botstein & Shortle (1985) "Strategies and applications of in vitro mutagenesis" *Science* 229:1193–1201; Carter (1986) "Site-directed mutagenesis" *Biochem. J.* 237:1–7; and Kunkel (1987) "The efficiency of oligonucleotide directed mutagenesis" in *Nucleic Acids & Molecular Biology* (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" *Proc. Natl. Acad. Sci. USA* 82:488–492; Kunkel et al. (1987) "Rapid and efficient site-specific mutagenesis without phenotypic selection" *Methods in Enzymol.* 154, 367–382; and Bass et al. (1988) "Mutant Trp repressors with new DNA-binding specificities" *Science* 242:240–245); oligonucleotide-directed mutagenesis (*Methods in Enzymol.* 100: 468–500 (1983); *Methods in Enzymol.* 154: 329–350 (1987); Zoller & Smith (1982) "Oligonucleotide-directed mutagenesis using M13-derived vectors: an efficient and general procedure for the production of point mutations in any DNA fragment" *Nucleic Acids Res.* 10:6487–6500; Zoller & Smith (1983) "Oligonucleotide-directed mutagenesis of DNA fragments cloned into M13 vectors" *Methods in Enzymol.* 100:468–500; and Zoller & Smith (1987) "Oligonucleotide-directed mutagenesis: a simple method using two oligonucleotide primers and a single-stranded DNA template" *Methods in Enzymol.* 154:329–350); phosphorothioate-modified DNA mutagenesis (Taylor et al. (1985) "The use of phosphorothioate-modified DNA in restriction enzyme reactions to prepare nicked DNA" *Nucl. Acids Res.* 13: 8749–8764; Taylor et al. (1985) "The rapid generation of oligonucleotide-directed mutations at high frequency using phosphorothioate-modified DNA" *Nucl. Acids Res.* 13: 8765–8787 (1985); Nakamaye & Eckstein (1986) "Inhibition of restriction endonuclease Nci I cleavage by phosphorothioate groups and its application to oligonucleotide-directed mutagenesis" *Nucl. Acids Res.* 14: 9679–9698; Sayers et al. (1988) "Y-T Exonucleases in phosphorothioate-based oligonucleotide-directed mutagenesis" *Nucl. Acids Res.* 16:791–802; and Sayers et al. (1988) "Strand specific cleavage of phosphorothioate-containing DNA by reaction with restriction endonucleases in the presence of ethidium bromide" *Nucl. Acids Res.* 16: 803–814); mutagenesis using gapped duplex DNA (Kramer et al. (1984) "The gapped duplex DNA approach to oligonucleotide-directed mutation construction" *Nucl. Acids Res.* 12: 9441–9456; Kramer & Fritz (1987) *Methods in Enzymol.* "Oligonucleotide-directed construction of mutations via gapped duplex DNA" 154:350–367; Kramer et al. (1988) "Improved enzymatic in vitro reactions in the gapped duplex DNA approach to oligonucleotide-directed construction of mutations" *Nucl. Acids Res.* 16: 7207; and Fritz et al. (1988) "Oligonucleotide-directed construction of mutations: a gapped duplex DNA procedure without enzymatic reactions in vitro" *Nucl. Acids Res.* 16: 6987–6999).

Additional suitable methods include point mismatch repair (Kramer et al. (1984) "Point Mismatch Repair" *Cell* 38:879–887), mutagenesis using repair-deficient host strains (Carter et al. (1985) "Improved oligonucleotide site-directed mutagenesis using M13 vectors" *Nucl. Acids Res.* 13: 4431–4443; and Carter (1987) "Improved oligonucleotide-directed mutagenesis using M13 vectors" *Methods in Enzymol.* 154: 382–403), deletion mutagenesis (Eghtedarzadeh & Henikoff (1986) "Use of oligonucleotides to generate large deletions" *Nucl. Acids Res.* 14: 5115), restriction-selection and restriction-selection and restriction-purification (Wells et al. (1986) "Importance of hydrogen-bond formation in stabilizing the transition state of subtilisin" *Phil. Trans. R. Soc. Lond.* A 317: 415–423), mutagenesis by total gene synthesis (Nambiar et al. (1984) "Total synthesis and cloning of a gene coding for the ribonuclease S protein" *Science* 223: 1299–1301; Sakamar and Khorana (1988) "Total synthesis and expression of a gene for the a-subunit of bovine rod outer segment guanine nucleotide-binding protein (transducin)" *Nucl. Acids Res.* 14: 6361–6372; Wells et al. (1985) "Cassette mutagenesis: an efficient method for generation of multiple mutations at defined sites" *Gene* 34:315–323; and Grundstrom et al. (1985) "Oligonucleotide-directed mutagenesis by microscale 'shot-gun' gene synthesis" *Nucl. Acids Res.* 13: 3305–3316), double-strand break repair (Mandecki (1986); Arnold (1993) "Protein engineering for unusual environments" *Current Opinion in Biotechnology* 4:450–455. "Oligonucleotide-directed double-strand break repair in plasmids of *Escherichia coli*: a method for site-specific mutagenesis" *Proc. Natl. Acad. Sci. USA,* 83:7177–7181). Additional details on many of the above methods can be found in *Methods in Enzymology* Volume 154, which also describes useful controls for trouble-shooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Certain U.S. applications provide additional details regarding various diversity generating methods, including "SHUFFLING OF CODON ALTERED GENES" by Patten et al. filed Sep. 28, 1999, (U.S. Ser. No. 09/407,800); "EVOLUTION OF WHOLE CELLS AND ORGANISMS BY RECURSIVE SEQUENCE RECOMBINATION", by del Cardayre et al. filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Sep. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-VARIED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g., "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549).

In brief, several different general classes of sequence modification methods, such as mutation, recombination, etc. are applicable to the present invention and set forth, e.g., in the references above. For example, any of these methods can be adapted to the present invention to evolve engineered genetic elements like the engineered biotin ligases and engineered biotin dependent glyphosate resistance polynucleotides, discussed herein, to produce new engineered genetic elements with improved properties. In addition, any split gene sequences (e.g., enhancer-linked split gene sequences, etc.), unencrypted nucleic acids that comprise split gene sequences, trans-splicing introns, toxic genetic elements, or the like are optionally modified to improve, e.g., splicing or activity according to any of these techniques or combinations of these techniques. Furthermore, nucleic acid sequences to be modified are optionally derived from various known or designed genetic elements available, e.g., from many public databases, such as Genbank®.

The following exemplify some of the different types of preferred formats for diversity generation in the context of the present invention, including, e.g., certain recombination based diversity generation formats.

Nucleic acids can be recombined in vitro by any of a variety of techniques discussed in the references above, including e.g., DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction. This process and many process variants is described in several of the references above, e.g., in Stemmer (1994) *Proc. Natl. Acad. Sci. USA* 91:10747–10751. Thus, for example, parental engineered genetic elements or the like are optionally digested with DNAse and then ligated or reassembled using the PCR to create the evolved enzymes of the invention.

Similarly, nucleic acids can be recursively recombined in vivo, e.g., by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references noted above. Thus, for example, two naturally occurring genetic elements are optionally recombined in vivo to produce an engineered genetic element with improved traits or properties.

Whole genome recombination methods can also be used in which whole genomes of cells or other organisms are recombined, optionally including spiking of the genomic recombination mixtures with desired library components (e.g., genes corresponding to the pathways of the present invention). These methods have many applications, including those in which the identity of a target gene is not known. Details on such methods are found, e.g., in WO 98/31837 by del Cardayre et al. "Evolution of Whole Cells and Organisms by Recursive Sequence Recombination;" and in, e.g., PCT/US99/15972 by del Cardayre et al., also entitled "Evolution of Whole Cells and Organisms by Recursive Sequence Recombination." For example, in one embodiment, the methods include introducing, e.g., a library of DNA fragments encoding unevolved and/or evolved genetic element into a plurality of host cells in which the fragments undergo recombination with segments of the genomes or episomes of the cells. Thereafter, the modified cells are screened or selected for one or more desired traits or properties.

Synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Details regarding such approaches are found in the references noted above, including, e.g., "OLIGONUCLEOTIDE MEDIATED NUCLEIC ACID RECOMBINATION" by Crameri et al., filed Sept. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-VARIED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202); "METHODS OF POPULATING DATA STRUCTURES FOR USE IN EVOLUTIONARY SIMULATIONS" by Selifonov and Stemmer (PCT/US00/01138), filed Jan. 18, 2000; and, e.g., "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579).

In silico methods of recombination can be effected in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis/gene reassembly techniques. This approach can generate random, partially random or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (e.g., based on cross-over site selection) as well as designed, pseudorandom or random recombination methods are described in "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) "METHODS OF POPULATING DATA STRUCTURES FOR USE IN EVOLUTIONARY SIMULATIONS" by Selifonov and Stemmer (PCT/US00/01138), filed Jan. 18, 2000; and, e.g., "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579). Extensive details regarding in silico recombination methods are found in these applications. This methodology is generally applicable to the present invention in providing for recombination of known genetic element sequences in silico and/ or the generation of corresponding nucleic acids or proteins.

Many methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. In one method employing a single-stranded template, the fragment population derived from the genomic library(ies) is annealed with partial, or, often approximately full length ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (e.g., if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. Additional details regarding this approach are found, e.g., in "SINGLE-STRANDED NUCLEIC ACID TEMPLATE-MEDIATED RECOMBINATION AND NUCLEIC ACID FRAGMENT ISOLATION" by Affholter, U.S. Ser. No. 09/656,549, filed Sep. 6, 2000.

In another approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library enriched sequences which hybridize to the probe. A library produced in this manner provides a desirable substrate for further diversification using any of the procedures described herein.

Any of the preceding general recombination formats can be practiced in a reiterative fashion (e.g., one or more cycles of mutation/recombination or other diversity generation methods, optionally followed by one or more selection methods) to generate a more diverse set of recombinant nucleic acids.

Mutagenesis employing polynucleotide chain termination methods have also been proposed (see, e.g., U.S. Pat. No. 5,965,408, "Method of DNA reassembly by interrupting synthesis" to Short, and the references above), and can be applied to the present invention. In this approach, double stranded DNAs corresponding to one or more genes sharing regions of sequence similarity are combined and denatured, in the presence or absence of primers specific for the gene. The single stranded polynucleotides are then annealed and incubated in the presence of a polymerase and a chain terminating reagent (e.g., ultraviolet, gamma or X-ray irradiation; ethidium bromide or other intercalators; DNA binding proteins, such as single strand binding proteins, transcription activating factors, or histones; polycyclic aromatic hydrocarbons; trivalent chromium or a trivalent chromium salt; or abbreviated polymerization mediated by rapid thermocycling; and the like), resulting in the production of partial duplex molecules. The partial duplex molecules, e.g., containing partially extended chains, are then denatured and reannealed in subsequent rounds of replication or partial replication resulting in polynucleotides which share varying degrees of sequence similarity and which are diversified with respect to the starting population of DNA molecules. Optionally, the products, or partial pools of the products, can be amplified at one or more stages in the process. Polynucleotides produced by a chain termination method, such as described above, are suitable substrates for any other described recombination format.

Diversity also can be generated in nucleic acids or populations of nucleic acids using a recombinational procedure termed "incremental truncation for the creation of hybrid enzymes" ("ITCHY") described in Ostermeier et al. (1999) "A combinatorial approach to hybrid enzymes independent of DNA homology" *Nature Biotech* 17:1205. This approach can be used to generate an initial a library of variants which optionally serves as a substrate for one or more in vitro or in vivo recombination methods. See, also, Ostermeier et al. (1999) "Combinatorial Protein Engineering by Incremental Truncation," *Proc. Natl. Acad. Sci. USA*, 96: 3562–67; Ostermeier et al. (1999), "Incremental Truncation as a Strategy in the Engineering of Novel Biocatalysts," *Biological and Medicinal Chemistry*, 7: 2139–44.

Mutational methods which result in the alteration of individual nucleotides or groups of contiguous or non-contiguous nucleotides can be favorably employed to introduce nucleotide diversity. For example, engineered genetic elements or the like are optionally created via such mutational methods. Many mutagenesis methods are found in the above-cited references; additional details regarding mutagenesis methods can be found in following, which can also be applied to the present invention.

For example, error-prone PCR can be used to generate nucleic acid variants. Using this technique, PCR is performed under conditions where the copying fidelity of the DNA polymerase is low, such that a high rate of point mutations is obtained along the entire length of the PCR product. Examples of such techniques are found in the references above and, e.g., in Leung et al. (1989) *Technique* 1:11–15 and Caldwell et al. (1992) *PCR Methods Applic.* 2:28–33. Similarly, assembly PCR can be used, in a process which involves the assembly of a PCR product from a mixture of small DNA fragments. A large number of different PCR reactions can occur in parallel in the same reaction mixture, with the products of one reaction priming the products of another reaction.

Oligonucleotide directed mutagenesis can be used to introduce site-specific mutations in a nucleic acid sequence of interest. Examples of such techniques are found in the references above and, e.g., in Reidhaar-Olson et al. (1988) *Science*, 241:53–57. Similarly, cassette mutagenesis can be used in a process that replaces a small region of a double stranded DNA molecule with a synthetic oligonucleotide cassette that differs from the native sequence. The oligonucleotide can contain, e.g., completely and/or partially randomized native sequence(s).

Recursive ensemble mutagenesis is a process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are found in Arkin & Youvan (1992) *Proc. Natl. Acad. Sci. USA* 89:7811–7815.

Exponential ensemble mutagenesis can be used for generating combinatorial libraries with a high percentage of unique and functional mutants. Small groups of residues in a sequence of interest are randomized in parallel to identify, at each altered position, amino acids which lead to functional proteins. Examples of such procedures are found in Delegrave & Youvan (1993) *Biotechnology Research* 11:1548–1552.

In vivo mutagenesis can be used to generate random mutations in any cloned DNA of interest by propagating the DNA, e.g., in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA. Such procedures are described in the references noted above.

Other procedures for introducing diversity into a genome, e.g. a bacterial, fungal, animal or plant genome can be used in conjunction with the above described and/or referenced methods. For example, in addition to the methods above, techniques have been proposed which produce nucleic acid multimers suitable for transformation into a variety of species (see, e.g., Schellenberger U.S. Pat. No. 5,756,316 and the references above). Transformation of a suitable host with such multimers, consisting of genes that are divergent with respect to one another, (e.g., derived from natural diversity or through application of site directed mutagenesis, error prone PCR, passage through mutagenic bacterial strains, and the like), provides a source of nucleic acid diversity for DNA diversification, e.g., by an in vivo recombination process as indicated above.

Alternatively, a multiplicity of monomeric polynucleotides sharing regions of partial sequence similarity can be transformed into a host species and recombined in vivo by the host cell. Subsequent rounds of cell division can be used to generate libraries, members of which, include a single, homogenous population, or pool of monomeric polynucleotides. Alternatively, the monomeric nucleic acid can be recovered by standard techniques, e.g., PCR and/or cloning, and recombined in any of the recombination formats, including recursive recombination formats, described above.

Methods for generating multispecies expression libraries have been described (in addition to the reference noted above, see, e.g., Peterson et al. (1998) U.S. Pat. No. 5,783, 431 "METHODS FOR GENERATING AND SCREENING NOVEL METABOLIC PATHWAYS," and Thompson, et al. (1998) U.S. Pat. No. 5,824,485 METHODS FOR GENERATING AND SCREENING NOVEL METABOLIC PATHWAYS) and their use to identify protein activities of interest has been proposed (In addition to the references noted above, see, Short (1999) U.S. Pat. No. 5,958,672 "PROTEIN ACTIVITY SCREENING OF CLONES HAVING DNA FROM UNCULTIVATED MICROORGANISMS"). Multispecies expression libraries include, in general, libraries comprising cDNA or genomic sequences from a plurality of species or strains, operably linked to appropriate regulatory sequences, in an expression cassette. The cDNA and/or genomic sequences are optionally randomly ligated to further enhance diversity. The vector can be a shuttle vector suitable for transformation and expression in more than one species of host organism, e.g., bacterial species, eukaryotic cells. In some cases, the library is biased by preselecting sequences which encode a protein of interest, or which hybridize to a nucleic acid of interest. Any such libraries can be provided as substrates for any of the methods herein described.

The above described procedures have been largely directed to increasing nucleic acid and/or encoded protein diversity. However, in many cases, not all of the diversity is useful, e.g., functional, and contributes merely to increasing the background of variants that must be screened or selected to identify the few favorable variants. In some applications, it is desirable to preselect or prescreen libraries (e.g., an amplified library, a genomic library, a cDNA library, a normalized library, etc.) or other substrate nucleic acids prior to diversification, e.g., by recombination-based mutagenesis procedures, or to otherwise bias the substrates towards nucleic acids that encode functional products. For example, in the case of antibody engineering, it is possible to bias the diversity generating process toward antibodies with functional antigen binding sites by taking advantage of in vivo recombination events prior to manipulation by any of the described methods. For example, recombined CDRs derived from B cell cDNA libraries can be amplified and assembled into framework regions (e.g., Jirholt et al. (1998) "Exploiting sequence space: shuffling in vivo formed complementarity determining regions into a master framework" *Gene* 215: 471) prior to diversifying according to any of the methods described herein.

Libraries can be biased towards nucleic acids which encode proteins with desirable enzyme activities. For example, after identifying a clone from a library which exhibits a specified activity, the clone can be mutagenized using any known method for introducing DNA alterations. A library comprising the mutagenized homologues is then screened for a desired activity, which can be the same as or different from the initially specified activity. An example of such a procedure is proposed in Short (1999) U.S. Pat. No. 5,939,250 for "PRODUCTION OF ENZYMES HAVING DESIRED ACTIVITIES BY MUTAGENESIS." Desired activities can be identified by any method known in the art. For example, WO 99/10539 proposes that gene libraries can be screened by combining extracts from the gene library with components obtained from metabolically rich cells and identifying combinations which exhibit the desired activity. It has also been proposed (e.g., WO 98/58085) that clones with desired activities can be identified by inserting bioactive substrates into samples of the library, and detecting bioactive fluorescence corresponding to the product of a desired activity using a fluorescent analyzer, e.g., a flow cytometry device, a CCD, a fluorometer, or a spectrophotometer.

Libraries can also be biased towards nucleic acids which have specified characteristics, e.g., hybridization to a selected nucleic acid probe. For example, application WO 99/10539 proposes that polynucleotides encoding a desired activity (e.g., an enzymatic activity, for example: a lipase, an esterase, a protease, a glycosidase, a glycosyl transferase, a phosphatase, a kinase, an oxygenase, a peroxidase, a hydrolase, a hydratase, a nitrilase, a transaminase, an amidase or an acylase) can be identified from among genomic DNA sequences in the following manner. Single stranded DNA molecules from a population of genomic DNA are hybridized to a ligand-conjugated probe. The genomic DNA can be derived from either a cultivated or uncultivated microorganism, or from an environmental sample. Alternatively, the genomic DNA can be derived from a multicellular organism, or a tissue derived therefrom. Second strand synthesis can be conducted directly from the hybridization probe used in the capture, with or without prior release from the capture medium or by a wide variety of other strategies known in the art. Alternatively, the isolated single-stranded genomic DNA population can be fragmented without further cloning and used directly in, e.g., a recombination-based approach, that employs a single-stranded template, as described above.

"Non-Stochastic" methods of generating nucleic acids and polypeptides are alleged in Short "Non-Stochastic Generation of Genetic Vaccines and Enzymes" WO 00/46344. These methods, including proposed non-stochastic polynucleotide reassembly and site-saturation mutagenesis methods be applied to the present invention as well. Random or semi-random mutagenesis using doped or degenerate oligonucleotides is also described in, e.g., Arkin and Youvan (1992) "Optimizing nucleotide mixtures to encode specific subsets of amino acids for semi-random mutagenesis" *Biotechnology* 10:297–300; Reidhaar-Olson et al. (1991) "Random mutagenesis of protein sequences using oligonucleotide cassettes" *Methods Enzymol.* 208:564–86; Lim and Sauer (1991) "The role of internal packing interactions in determining the structure and stability of a protein" *J. Mol. Biol.* 219:359–76; Breyer and Sauer (1989) "Mutational analysis of the fine specificity of binding of monoclonal antibody 51F to lambda repressor" *J. Biol. Chem.* 264:13355–60); and "Walk-Through Mutagenesis" (Crea, R; U.S. Pat. Nos. 5,830,650 and 5,798,208, and EP Patent 0527809 B1.

It will readily be appreciated that any of the above described techniques suitable for enriching a library prior to diversification can also be used to screen the products, or libraries of products, produced by the diversity generating methods.

Kits for mutagenesis, library construction and other diversity generation methods are also commercially available. For example, kits are available from, e.g., Stratagene (e.g., QuickChange™ site-directed mutagenesis kit; and Chameleon™ double-stranded, site-directed mutagenesis kit), Bio/Can Scientific, Bio-Rad (e.g., using the Kunkel method described above), Boehringer Mannheim Corp., Clonetech Laboratories, DNA Technologies, Epicentre Technologies (e.g., 5 prime 3 prime kit); Genpak Inc, Lemargo Inc, Life Technologies (Gibco BRL), New England Biolabs, Pharmacia Biotech, Promega Corp., Quantum Biotechnologies, Amersham International plc (e.g., using the Eckstein method above), and Anglian Biotechnology Ltd (e.g., using the Carter/Winter method above).

The above references provide many mutational formats, including standard mutagenesis methods, recombination, recursive recombination, recursive mutation and combinations or recombination with other forms of mutagenesis, as well as many modifications of these formats. Regardless of the diversity generation format that is used, the nucleic acids of the invention can be recombined (with each other, or with related (or even unrelated) sequences) to produce a diverse set of recombinant nucleic acids, including, e.g., sets of homologous nucleic acids, as well as corresponding polypeptides. Any of these diversity generating methods can be combined, in any combination selected by the user, to produce nucleic acid diversity, which may be screened for using any available screening method.

Non-Overlapping Gene Sequence Recombination Targets

Virtually any nucleic acid can be recombined, or otherwise modified, by the methods described in this disclosure. No attempt is made to identify the hundreds of thousands of known nucleic acids. However, certain preferred target sequences for non-overlapping gene sequence mediated-recombination include inhibitors of transcription or toxins of crop pests (e.g., insects, fungi, weed plants, etc.), recombinases (e.g., Cre-lox, VDJ, etc.), integrases (e.g., λ integrase), and the like. As discussed further below, common sequence repositories for known proteins include GenBank®, Entrez®, EMBL, DDBJ, GSDB, NDB and the NCBI. Other repositories can easily be identified by searching the internet.

Post-Modification Screening Techniques

The precise screening technique that is used in the diversity generating or modification methods (e.g., recombination, mutagenesis, or the like) disclosed herein is not a critical aspect of the invention. In general, one of skill can practice appropriate screening or selection methods by reference to the activity to be selected for.

In any case, one or more diversity generation or modification cycles are usually followed by at least one cycle of screening or selection for molecules having a desired property or characteristic. If a modification cycle is performed in vitro, the products of the modification (e.g., recombinant sequences, etc.) are sometimes introduced into cells before the screening step. Modified sequences can also be linked to an appropriate vector or other regulatory sequence before screening. Alternatively, modified products generated in vitro are sometimes packaged in viruses (e.g., bacteriophage) before screening. If nucleic acid sequence modification is performed in vivo, the products can sometimes be screened in the cells in which modification occurred. In other applications, modified sequences are extracted from the cells, and optionally packaged as viruses, before screening.

The nature of screening or selection depends on what property or characteristic is to be acquired or the property or characteristic for which improvement is sought, and many examples are discussed below. It is not usually necessary to understand the molecular basis by which particular products of diversity generation or modification (e.g., recombinant sequences, mutant sequences, etc.) have acquired new or improved properties or characteristics relative to the starting substrates. For example, a gene can have many component sequences, each having a different intended role (e.g., coding sequence, regulatory sequences, targeting sequences, stability-conferring sequences, subunit sequences and sequences affecting integration). Each of these component sequences can be varied and recombined, or otherwise modified, simultaneously. Screening/selection can then be performed, for example, for modified sequences that have increased ability to confer activity upon a cell without the need to attribute such improvement to any of the individual component sequences of the vector.

Depending on the particular screening protocol used for a desired property, initial round(s) of screening can sometimes be performed using bacterial cells due to high transfection efficiencies and ease of culture. However, bacterial expression is often not practical or desired, and yeast, fungal or other eukaryotic systems are also used for library expression and screening. Similarly, other types of screening which are not amenable to screening in bacterial or simple eukaryotic library cells, are performed in cells selected for use in an environment close to that of their intended use. Final rounds of screening can be performed in the precise cell type of intended use.

If further improvement in a property is desired, at least one and usually a collection of modified sequences surviving a first round of screening/selection are subject to a further round of diversity generation (e.g., recombination, mutagenesis, or the like). For example, these sequences can be recombined with each other or with exogenous sequences representing the original substrates or further variants thereof. Again, modification can proceed in vitro or in vivo. To illustrate with recombination as the selected diversity generating technique, if the previous screening step identifies desired modified sequences as components of cells, the components can be subjected to, e.g., further recombination in vivo, or can be subjected to, e.g., further recombination in vitro, or can be isolated before performing, e.g., a round of in vitro recombination. Conversely, if the previous screening step identifies desired modified sequences in naked form or as components of viruses, these sequences can be introduced into cells to perform, e.g., a round of in vivo recombination. The second round of modification, irrespective how performed, generates further modified sequences which encompass additional diversity than is present in modified sequences resulting from previous rounds.

The second round of diversity generation or modification can be followed by a further round of screening/selection according to the principles discussed above for the first round. The stringency of screening/selection can be increased between rounds. Also, the nature of the screen and the property being screened for can vary between rounds if improvement in more than one property is desired or if acquiring more than one new property is desired. Additional rounds of modification and screening can then be performed until the modified sequences have sufficiently evolved to acquire the desired new or improved property or function.

Target Gene Sequence Preparation

An initial inquiry applicable to the methods of the present invention includes determining the sequence of nucleotides in target sequences, e.g., in genes to be split between two parental organisms or between a host organism and a vector, in engineered genetic elements, or in non-overlapping gene sequences. Thereafter, polynucleotides such as gap nucleic acid sequences can be designed based upon this sequence information. Target sequences can be prepared using various methods or combinations thereof, including certain DNA synthetic techniques (e.g., mononucleotide-and/or trinucleotide-based synthesis, reverse-transcription, etc.), DNA amplification, restriction enzyme digestion, etc.

Split gene sequences can be designed to ensure that trans-splicing will be accurately targeted. See Puttaraju, M. et al. (1999) *Nat. Biotech.* 17, 246–252. For example, a gene encoding a desired product, e.g., a growth hormone, Bt toxin, etc. can be split, e.g., between two coding subsequences. A first coding subsequence can include a target binding domain that is complementary to a downstream intron (e.g., βhCG6 intron 1) of the second coding subsequence. The first coding sequence can also include a spacer region, a branch point sequence (e.g., a UACUAAC yeast consensus branch point sequence), a polypyrimidine tract, and an AG dinucleotide at the 3' splice site immediately upstream of the coding region of the first subsequence. A similar construct has been utilized to achieve very precise trans-splicing. Id. Promoter and transcriptional terminator sequences that control the expression of the coding regions can also be included. For example, if the coding sequences are to be expressed constitutively throughout a plant, the 35S RNA promoter from the cauliflower mosaic virus can be used. Cell-specific specific promoters are also available and known to those of skill. Similarly, sequences can be recombined and selected for desired splicing.

Target coding sequences to be split according to the methods of the present invention can be derived from any type of organism. Plant-related target sequences, however, include those that confer herbicide-resistance to permit lower treatment with herbicides like glyphosate, and various suphonylurea, phosphinothricin, and bromoxynil compounds. Other target sequences include those that provide plants with insect resistance (e.g., δ-endotoxin from *Bacillus thuringiensis*), viral resistance, male sterility, and the like.

Gene Sequence Information, Selection, and Design

Searchable sequence information available from various nucleic acid databases can be utilized during the nucleic acid sequence selection and/or design processes. Genbank®, Entrez®, EMBL, DDBJ, GSDB, NDB, and the NCBI are examples of public database/search services that can be accessed. These databases are generally available via the internet or on a contract basis from a variety of companies specializing in genomic information generation and/or storage. These and other helpful resources are readily available and known to those of skill.

The sequence of a polynucleotide to be used in any of the methods of the present invention can also be readily determined using techniques well-known to those of skill, including Maxam-Gilbert, Sanger Dideoxy, and Sequencing by Hybridization methods. For general descriptions of these processes consult, e.g., Stryer, L., Biochemistry (4th Ed.) W. H. Freeman and Company, New York, 1995 (Stryer) and Lewin, B. Genes VI Oxford University Press, Oxford, 1997 (Lewin). See also, Maxam, A. M. and Gilbert, W. (1977) "A New Method for Sequencing DNA," Proc. Natl. Acad. Sci. 74:560–564, Sanger, F. et al. (1977) "DNA Sequencing with Chain-Terminating Inhibitors," Proc. Natl. Acad. Sci. 74:5463–5467, Hunkapiller, T. et al. (1991) "Large-Scale and Automated DNA Sequence Determination," Science 254:59–67, and Pease, A. C. et al. (1994) "Light-Generated Oligonucleotide Arrays for Rapid DNA Sequence Analysis," Proc. Natl. Acad. Sci. 91:5022–5026.

In certain aspects, the present invention also optionally includes aligning target nucleic acid sequences and/or searching those sequences for specific subsequences. For example, an object of methods of recombining non-overlapping gene sequences herein is to avoid reassembling original gene sequences. The alignment and comparison of fragments of a gene sequence to be recombined, in this manner, can be utilized to ensure that no regions of overlap, i.e., homology or complementarity exist among the fragments to be recombined. Sequence comparison and alignment can also be of use in the process of designing gap nucleic acids which are sequences that include regions that are homologous or substantially homologous with at least two non-overlapping gene sequences. Additionally, as discussed further below, split genes can be created, e.g., upon digestion by certain restriction endonucleases that generate blunt ends. As such, the process of designing split genes can involve searching a particular gene sequence to be split for specific restriction sites.

In the processes of sequence comparison and homology determination, one sequence, e.g., one fragment or subsequence of a gene sequence to be recombined, can be used as a reference against which other test nucleic acid sequences are compared. This comparison can be accomplished with the aid of a sequence comparison instruction set, i.e., algorithm, or by visual inspection. When an algorithm is employed, test and reference sequences are input into a computer, subsequence coordinates are designated, as necessary, and sequence algorithm program parameters are specified. The algorithm then calculates the percent sequence identity for the test nucleic acid sequence(s) relative to the reference sequence, based on the specified program parameters. Integrated systems that are relevant to the invention are discussed further, infra.

For purposes of the present invention, suitable sequence comparisons can be executed, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wisc.), or by visual inspection. See generally, Current Protocols in Molecular Biology, F. M. Ausubel et al., eds., Current Protocols, a joint venture between Greene Publishing Associates, Inc. and John Wiley & Sons, Inc., (supplemented through 1999), supra).

One example search algorithm that is suitable for determining percent sequence identity and sequence similarity is the Basic Local Alignment Search Tool (BLAST) algorithm, which is described in Altschul et al., J. Mol. Biol. 215:403–410 (1990). Software for performing BLAST analyses is publicly available through the National Center for Biotechnology Information (http://www.ncbi.nlm.nih.gov/).

Target Sequence Acquisition

After sequence information has been obtained as described above, that information can be used to design and synthesize target nucleic acid sequences corresponding to, e.g., split gene sequences, enhancer-linked split gene sequences, trans-acting transcription factor sequences, engineered genetic elements, non-overlapping gene sequences, and gap nucleic acids. These sequences can be synthesized utilizing various solid-phase strategies involving mononucleotide- and/or trinucleotide-based phosphoramidite coupling chemistry. In these approaches, nucleic acid sequences are synthesized by the sequential addition of activated monomers and/or trimers to an elongating polynucleotide chain. See e.g., Caruthers, M. H. et al. (1992) Meth. Enzymol. 211:3–20.

In the formats involving trimers, trinucleotide phosphoramidites representing codons for all 20 amino acids are used to introduce entire codons into the growing oligonucleotide sequences being synthesized. The details on synthesis of trinucleotide phoshoramidites, their subsequent use in oligonucleotide synthesis, and related issues are described in, e.g., Virnekas, B., et al. (1994) Nucleic Acids Res., 22, 5600–5607, Kayushin, A. L. et al. (1996) Nucleic Acids Res., 24, 3748–3755, Huse, U.S. Pat. No. 5,264,563 "PROCESS FOR SYNTHESIZING OLIGONUCLEOTIDES WITH RANDOM CODONS," Lyttle et al., U.S. Pat. No. 5,717,085 "PROCESS FOR PREPARING CODON AMIDITES," Shortle et al., U.S. Pat. No. 5,869,644 "SYNTHESIS OF DIVERSE AND USEFUL COLLECTIONS OF OLIGONUCLEOTIDES," Greyson, U.S. Pat. No. 5,789,577 "METHOD FOR THE CONTROLLED SYNTHESIS OF POLYNUCLEOTIDE MIXTURES WHICH ENCODE DESIRED MIXTURES OF PEPTIDES," and Huse, WO 92/06176 "SURFACE EXPRESSION LIBRARIES OF RANDOMIZED PEPTIDES."

The chemistry involved in these synthetic methods is known by those of skill. In general, they utilize phosphoramidite solid-phase chemical synthesis in which the 3' ends of nucleic acid substrate sequences are covalently attached to a solid support, e.g., controlled pore glass. The 5' protecting groups can be, e.g., a triphenylmethyl group, such as, dimethoxyltrityl (DMT) or monomethyoxytrityl, a carbonyl-containing group, such as, 9-fluorenylmethyloxycarbonyl (FMOC) or levulinoyl, an acid-clearable group, such as, pixyl, a fluoride-cleavable alkylsilyl group, such as, tert-butyl dimethylsilyl (T-BDMSi), triisopropyl silyl, or trimethylsilyl. The 3' protecting groups can be, e.g., β-cyanoethyl groups.

These formats are optionally performed in an integrated automated synthesizer system that automatically performs the synthetic steps. See also, Integrated Systems, infra. This aspect includes inputting character string information into a computer, the output of which then directs the automated synthesizer to perform the steps necessary to synthesize the desired nucleic acid sequences. Automated synthesizers are available from many commercial suppliers including PE Biosystems and Beckman Instruments, Inc.

To further ensure that target gene sequences, e.g., non-overlapping or split gene sequences are ultimately obtained, certain techniques can be utilized following DNA synthesis. For example, gel purification is one method that can be used to purify synthesized oligonucleotides. High-performance liquid chromatography can be similarly employed. Furthermore, translational coupling can be used to assess gene functionality, e.g., to test whether full-length sequences such as engineered genetic elements are generated. In this process, the translation of a reporter protein, e.g., green fluorescent protein or β-galactosidase is coupled to that of the target gene product. This enables one to distinguish, e.g., full-length engineered genetic elements from those that contain deletions or frame shifts. The subsequent selection of desired traits or properties of target gene sequences is discussed further, supra.

In lieu of synthesizing the desired sequences, essentially any nucleic acid is optionally custom ordered from any of a variety of commercial sources, such as The Midland Certified Reagent Company (mcrc@oligos.com), The Great American Gene Company (www.genco.com), ExpressGen, Inc. (www.expressgen.com), Operon Technologies, Inc. (www.operon.com), and many others.

Target nucleic acid sequences, e.g., split or non-overlapping gene sequences can be derived from expression products, e.g., mRNAs expressed from genes within a cell of a plant or other organism. A number of techniques are available for detecting RNAs. For example, northern blot hybridization is widely used for RNA detection, and is generally taught in a variety of standard texts on molecular biology, including Ausubel, Sambrook, and Berger, supra. Furthermore, one of skill will appreciate that essentially any RNA can be converted into a double stranded DNA using a reverse transcriptase enzyme and a polymerase. See, Ausubel, Sambrook and Berger. Messenger RNAs can be detected by converting, e.g., mRNAs into cDNAs, which are subsequently detected in, e.g., a standard "Southern blot" format.

Examples of techniques sufficient to direct persons of skill through in vitro amplification methods, useful e.g., for amplifying synthesized split gene sequences, non-overlapping gene sequences, gap nucleic acids, or for reassembling genes comprising non-overlapping gene sequences, include the polymerase chain reaction (PCR), the ligase chain reaction (LCR), Qβ-replicase amplification, and other RNA polymerase mediated techniques (e.g., NASBA). These techniques are found in Ausubel, Sambrook, and Berger, as well as in Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal of NIH Research* (1991) 3, 81–94; Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al. (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. Improved methods of amplifying large nucleic acids, e.g., engineered genetic elements, by PCR are summarized in Cheng et al. (1994) *Nature* 369: 684–685 and the references therein, in which PCR amplicons of up to 40kb are generated.

In one preferred method, assembled sequences are checked for incorporation of non-overlapping gene sequences. This can be done by cloning and sequencing the nucleic acids, and/or by restriction digestion, e.g., as essentially taught in Ausubel, Sambrook, and Berger, supra. In addition, sequences can be PCR amplified and sequenced directly. Thus, in addition to, e.g., Ausubel, Sambrook, Berger, and Innis, additional PCR sequencing methodologies are also particularly useful. For example, direct sequencing of PCR generated amplicons by selectively incorporating boronated nuclease resistant nucleotides into the amplicons during PCR and digestion of the amplicons with a nuclease to produce sized template fragments has been performed (Porter et al. (1997) *Nucleic Acids Res.* 25(8):1611–1617).

Aside from directly synthesizing, e.g., split gene sequences and nonoverlapping gene sequences, as described above, certain restriction endonucleases can also be used to generate these sequences. For example, populations of specific genes of interest can be obtained, e.g., from an niRNA population which has been reverse-transcribed and amplified as mentioned, supra. Uniform sets of split gene and non-overlapping gene sequences can be created from these cDNA populations upon digestion, e.g., with blunt cutting restriction endonucleases (e.g., Alu I (AG↓CT), Dra I (TTT↓AAA), Eco RV (GAT↓ATC), Hae III (GG↓CC), Hind II (GT(T,C)↓(A,G)AC), Hpa I (GTT↓AAC), Mlu NI (TGG↓CCA), Nru I (TCG↓CGA), Pvu II (CAG↓CTG), Rsa I (GT↓AC), Sca I (AGT↓ACT), Sma I (CCC↓GGG), Ssp I (AAT↓ATT), Stu I (AGG↓CCT), Swa I (ATTT↓AAAT), and the like). Furthermore, the sequence information derived, e.g., as described supra, can be referenced to determine the number of fragments to be generated upon the digestion of a particular gene sequence. Various algorithms, also mentioned supra, can be helpful in searching for and determining the frequency of occurrence of restriction sites in a gene sequence, which information is useful in the design of both split gene and non-overlapping gene sequences.

Introduction of Nucleic Acid Sequences into the Cells of Organisms of Interests

In certain embodiments of the present invention, nucleic acid sequences are introduced into the cells of particular organisms of interest, including plants and animals. For example, split gene sequences, e.g., split herbicide resistance genes (FIG. 2), split toxic gene sequences (FIGS. 1 and 3), and the like can be introduced into the genomes of two parental organisms, e.g., corn, wheat, or other commercially important crops, e.g., for the ultimate production of hybrid progeny, for the creation of libraries of split genes, and the like. Similarly, enhancer-linked split gene sequences, trans-acting factors, engineered genetic elements, and recombined non-overlapping gene sequences can also be introduced into various organisms.

As applied to the present invention, upon identification of particular nucleic acids which encode, e.g., products of desirable quantitative traits (see, Edwards, et al. (1987) *Genetics* 115:113) or other genes or loci of interest, it is desirable to clone nucleic acids which are genetically linked to DNAs encoding these products for transduction into cells (e.g., coding sequences for the desired expression products, or genetically linked coding or non-coding sequences), especially to make, e.g., transgenic plants. The cloned sequences are also useful as molecular tags for selected plant strains, e.g., to identify parentage, and are further useful for encoding expression products, including nucleic acids and polypeptides.

A DNA linked to a locus encoding an expression product, e.g., a split gene sequence, an engineered genetic element, etc., is introduced into plant cells, either in culture or in organs of a plant, e.g., leaves, stems, fruit, seed, etc. The expression of natural or synthetic nucleic acids encoded by nucleic acids linked to expression product or target coding nucleic acids can be achieved by operably linking a cloned nucleic acid of interest, such as an expression product or a genetically linked nucleic acid, to a promoter, incorporating the construct into an expression vector and introducing the vector into a suitable host cell. Alternatively, an endogenous promoter linked to the nucleic acids can be used.

Cloning of Expression Product Sequences into Bacterial Hosts

There are several well-known methods of introducing target nucleic acids into bacterial cells, any of which may be used in the present invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAexpress Expression System™ from Qiagen). The isolated and purified plasmids are then further manipulated to produce other plasmids, used to transfect plant cells or incorporated into Agrobacterium tumefaciens related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, *Gene* 8:81 (1979); Roberts, et al., *Nature,* 328:731 (1987); Schneider, B., et al., *Protein Expr. Purif.* 6435:10 (1995); Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA Second Edition Scientific American Books, N.Y.*

Transfecting and Manipulating Plant Cells

Methods of transducing plant cells with nucleic acids are generally available and known by those of skill. In addition to Ausubel, Sambrook, and Berger, supra, useful general references for plant cell cloning, culture and regeneration include Payne include Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). A variety of Cell culture media are described in Atlas and Parks (eds) The Handbook of Microbiological Media (1993) CRC Press, Boca Raton, Fla. (Atlas). Additional information for plant cell culture is found in available commercial literature such as the *Life Science Research Cell Culture Catalogue* (1999) from Sigma-Aldrich, Inc (St Louis, Mo.) (Sigma-LSRCCC) and, e.g., the *Plant Culture Catalogue* and supplement (1999) also from Sigma-Aldrich, Inc (St Louis, Mo.) (Sigma-PCCS).

The various nucleic acid constructs of the invention, e.g., split gene sequences, engineered genetic elements, recombined non-overlapping gene sequences, etc., can be introduced into plant cells, either in culture or in the organs of a plant by a variety of conventional techniques. For example, the DNA construct can be introduced directly into the genomic DNA of the plant cell using techniques such as electroporation and microinjection of plant cell protoplasts, or the DNA constructs can be introduced directly to plant cells using ballistic methods, such as DNA particle bombardment. Alternatively, the DNA constructs are combined with suitable T-DNA flanking regions and introduced into a conventional *A. tumefaciens* host vector. The virulence functions of the *A. tumefaciens* host direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski, et al. (1984) *EMBO J.* 3:2717. Electroporation techniques are described in Fromm, et al. (1985) *Proc. Nat'l. Acad. Sci. USA* 82:5824. Ballistic transformation techniques are described in Klein, et al. (1987) *Nature* 327:70–73.

*A. tumefaciens*-mediated transformation techniques, including disarming and use of binary vectors, are also well described in the scientific literature. See, for example Horsch, et al. (1984) *Science* 233:496–498, and Fraley, et al. (1983) *Proc. Nat'l. Acad. Sci. USA* 80:4803. Agrobacterium-mediated transformation is a preferred method of transformation of dicots.

To use isolated sequences corresponding to or linked to target nucleic acid sequences in the above techniques, recombinant DNA vectors suitable for transformation of plant cells are prepared. A DNA sequence coding for the desired MRNA, polypeptide, or non-expressed sequence is transduced into the plant. Where the sequence is expressed, the sequence is optionally combined with transcriptional and translational initiation regulatory sequences that will direct the transcription of the sequence from the gene in the intended tissues of the transformed plant.

Promoters, in nucleic acids linked to loci identified by detecting expression products, are identified, e.g., by analyzing the 5' sequences upstream of a coding sequence in linkage disequilibrium with the loci. Optionally, such promoters will be associated with a desirable quantitative trait. Sequences characteristic of promoter sequences can be used to identify the promoter. Sequences controlling eukaryotic gene expression have been extensively studied. For instance, promoter sequence elements include the TATA box consensus sequence (TATAAT), which are usually 20 to 30 base pairs upstream of a transcription start site. In most instances the TATA box aids in accurate transcription initiation. In plants, further upstream from the TATA box, at positions −80 to −100, there is typically a promoter element with a series of adenines surrounding the trinucleotide G (or T) N G. See, e.g., J. Messing, et al., in *Genetic Engineering in Plants,* pp. 221–227 (Kosage, Meredith and Hollaender, eds. (1983)). A number of methods are known to those of skill in the art for identifying and characterizing promoter regions in plant genomic DNA. See, e.g., Jordano, et al. (1989) *Plant Cell* 1:855–866; Bustos, et al. (1989) *Plant Cell* 1:839–854; Green, et al. (1988) *EMBO J.* 7:4035–4044; Meier, et al. (1991) *Plant Cell* 3:309–316; and Zhang, et al. (1996) *Plant Physiology* 110:1069–1079.

In construction of recombinant expression cassettes of the invention, a plant promoter fragment is optionally employed which directs expression of a target nucleic acid, e.g., split gene sequences, engineered genetic elements, etc., in any or all tissues of a regenerated plant. Examples of constitutive promoters include the cauliflower mosaic virus (CaMV) 35S transcription initiation region, the 1'- or 2'-promoter derived from T-DNA of *A. tumafaciens*, and other transcription initiation regions from various plant genes known to those of skill. Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers.

Any of a number of promoters which direct transcription in plant cells can be suitable. The promoter can be either constitutive or inducible. In addition to the promoters noted above, promoters of bacterial origin that operate in plants include the octopine synthase promoter, the nopaline synthase promoter and other promoters derived from native Ti plasmids. See, Herrara-Estrella et al. (1983) *Nature*, 303:209–213. As mentioned above, viral promoters include the 35S and 19S RNA promoters of cauliflower mosaic virus. See, Odell et al. (1985) *Nature*, 313:810–812. Other plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) *EMBO J.* 7:3315–3327.

If polypeptide expression is desired, e.g., when a toxic polypeptide is sought, a polyadenylation region at the 3'-end of the coding region is typically included. The polyadenylation region can be derived from the natural gene, from a variety of other plant genes, or from T-DNA.

The vector comprising the sequences (e.g., promoters or coding regions) from genes encoding target nucleic acids of the invention can comprise a nucleic acid subsequence which confers a selectable phenotype on plant cells. The vector comprising the sequence optionally comprises a marker gene that confers a selectable phenotype on plant cells. For example, the marker may encode biocide tolerance, particularly antibiotic tolerance, such as tolerance to kanamycin, G418, bleomycin, hygromycin, or herbicide tolerance, such as tolerance to chlorosluforon, or phosphinothricin (the active ingredient in the herbicides bialaphos and Basta). For example, crop selectivity to specific herbicides can be conferred by engineering genetic elements into crops which encode appropriate herbicide metabolizing enzymes from other organisms, such as microbes. See, Padgette et al. (1996) "New Weed Control Opportunities: Development of Soybeans with a Round UP Ready™ Gene" In: *Herbicide-Resistant Crops* (Duke, ed.), pp 53–84, CRC Lewis Publishers, Boca Raton (Padgette); and Vasil (1996) "Phosphinothricin-Resistant Crops" In: *Herbicide-Resistant Crops* (Duke, ed.), pp 85–91, CRC Lewis Publishers, Boca Raton) (Vasil). Transgenic plants have been engineered to express a variety of herbicide tolerance/metabolizing genes, from a variety of organisms. For example, acetohydroxy acid synthase, which has been found to make plants which express this enzyme resistant to multiple types of herbicides, has been cloned into a variety of plants (see, e.g., Hattori, J., et al. (1995) *Mol. Gen. Genet.* 246(4: 419). Other genes that confer tolerance to herbicides include: a gene encoding a chimeric protein of rat cytochrome P4507A1 and yeast NADPH-cytochrome P450 oxidoreductase (Shiota, et al. (1994) *Plant Physiol.* 106(1)17, genes for glutathione reductase and superoxide dismutase (Aono, et al. (1995) *Plant Cell Physiol.* 36(8):1687, and genes for various phosphotransferases (Datta, et al. (1992) *Plant Mol. Biol.* 20(4):619. Similarly, crop selectivity can be conferred by altering the gene coding for an herbicide target site so that the altered protein is no longer inhibited by the herbicide (Padgette). Several such crops have been engineered with specific microbial enzymes for confer selectivity to specific herbicides (Vasil).

Further, target nucleic acids which can be cloned and introduced into plants to modify or complement expression of a gene, including a silenced gene, a dominant gene, and additive gene or the like, can be any of a variety of constructs, depending on the particular application. Thus, a nucleic acid encoding a cDNA expressed from an identified gene can be expressed in a plant under the control of a heterologous promoter. Similarly, a nucleic acid encoding a trans-acting transcription factor that regulates an enhancer-linked split gene sequence identified by the methods herein, or that encodes any other moiety affecting transcription, can be cloned and transduced into a plant. Methods of identifying such factors are replete throughout the literature. For a basic introduction to genetic regulation, see, Lewin (1997) *Genes VI* Oxford University Press Inc., NY (Lewin), and the references cited therein.

Stable plants producing one or more split gene sequence (s) can be produced, with the unencrypted sequence being produced only upon transduction with a vector which encodes one or more additional split gene sequences.

Regeneration of Transgenic Plants

Transformed plant cells which are derived by any of the above transformation techniques can be cultured to regenerate a whole plant which possesses the transformed genotype and thus the desired phenotype. Such regeneration techniques rely on the manipulation of certain phytohormones in a tissue culture growth medium, typically relying on a biocide and/or herbicide marker which has been introduced together with the desired nucleotide sequences. Plant regeneration from cultured protoplasts is described in Evans, et al., *Protoplasts Isolation and Culture, Handbook of Plant Cell Culture*, pp. 124–176, Macmillian Publishing Company, New York, (1983); and Binding, *Regeneration of Plants, Plant Protoplasts*, pp. 21–73, CRC Press, Boca Raton, (1985). Regeneration can also be obtained from plant callus, explants, somatic embryos (Dandekar, et al., *J. Tissue Cult. Meth.* 12:145 (1989); McGranahan, et al., *Plant Cell Rep.* 8:512 (1990)), organs, or parts thereof. Such regeneration techniques are described generally in Klee, et al. (1987) *Ann. Rev. Plant Phys.* 38:467–486.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Compositions

The present invention provides various compositions including libraries of split gene sequence populations. These libraries collectively include a plurality of split gene sequence member types in which combinations or subcombinations of those member types collectively correspond to complete genetic elements, e.g., genes.

The invention additionally relates to a composition that includes libraries of enhancer-linked split gene sequence populations. These libraries collectively include a plurality of enhancer-linked split gene sequence member types, each regulated by a different trans-acting transcription factor in which combinations or subcombinations of the plurality of enhancer-linked split gene sequence member types collectively correspond to complete genetic elements. This composition optionally includes a trans-acting transcription factor corresponding to one of the two or more populations of enhancer-linked split gene sequences that can regulate the enhancer-linked split gene sequences of another population. This composition can also optionally include a first trans-acting transcription factor that corresponds to a first population of enhancer-linked split gene sequences that regulates the enhancer-linked split gene sequences of a second population, and a second trans-acting transcription factor that corresponds to the second population of enhancer-linked split gene sequences that regulates the enhancer-linked split gene sequences of the first population.

The invention also provides compositions that include libraries of gap nucleic acids. The libraries of gap nucleic acids include a plurality of gap nucleic acid member types in which each gap nucleic acid member type includes subsequence identity or complementarity with at least two split gene sequence member types.

The various composition members, i.e., the split gene sequences, the enhancer-linked split gene sequences, the trans-acting transcription factor sequences, the non-overlapping gene sequences, and the gap nucleic acids, can be cloned. As mentioned above, assorted cloning techniques are well-known. See e.g., Ausubel, Sambrook, and Berger, supra. A wide variety of cloning kits and associated products are commercially available from, e.g., Pharmacia Biotech, Stratagene, Sigma-Aldrich Co., Novagen, Inc., Fermentas, and 5 Prime→3Prime, Inc.

System Integration

As noted, supra, an initial inquiry that can be apply to the methods of the present invention includes determining the sequence of nucleotides in target sequences, e.g., genes to be split. Additionally, gap nucleic acid sequences can be designed based upon non-overlapping gene sequence information. As such, automated sequencing and sequence selection involving the alignment and search of nucleic acid sequences can be performed with the assistance of a computer and sequence alignment and comparison software in an integrated system. Target DNA sequences can then optionally be synthesized as an additional component of the integrated systems provided by the present invention. Other important integrated system components, however, can also provide for high-throughput screening assays, in addition to the coupling of such assays to oligonucleotide selection and recombination, e.g., recombined non-overlapping gene sequences.

In the high-throughput assays of the invention, it is possible to screen up to several thousand different recombination products in a single day. For example, each well of a microtiter plate can be used to run a separate assay, or, if concentration or incubation time effects are to be observed, every 5–10 wells can test a single product. Thus, a single standard microtiter plate can assay about 100 (e.g., 96) reactions. If 1536 well plates are used, then a single plate can easily assay from about 100 to approximately 1500 different reactions. It is possible to assay several different plates per day; assay screens for up to about 6,000–20,000 different assays (i.e., involving different nucleic acids, encoded proteins, concentrations, etc.) are possible using the integrated systems of the invention. More recently, microfluidic approaches to reagent manipulation have been developed, e.g., by Caliper Technologies (Mountain View, Calif.).

A number of well-known robotic systems have also been developed for solution phase chemistries useful in assay systems that are applicable to the present invention. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Beckman, Fullerton, Calif.) which mimic the manual synthetic operations performed by a scientist. Any of the above devices are suitable for use with the present invention, e.g., for high-throughput screening of molecules assembled from the various nucleic acid sequence sets described herein. The nature and implementation of modifications to these devices (if any) so that they can operate as discussed herein with reference to the integrated system will be apparent to persons skilled in the relevant art.

High-throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high-throughput. Thus, for example, Zymark Corp. provides technical bulletins describing screening systems for detecting the modulation of gene transcription, ligand binding, and the like.

Integrated systems for assay analysis in the present invention optionally include a digital computer with high-throughput liquid control software, image analysis software, data interpretation software, a robotic liquid control armature for transferring, e.g., split gene sequence solutions, engineered genetic element solutions, non-overlapping gene sequence compositions, and gap nucleic acid compositions from a source to a destination operably linked to the digital computer, an input device (e.g., a computer keyboard) for entering data to the digital computer to control high-throughput liquid transfer by the robotic liquid control armature.

These assay systems can also include integrated systems incorporating nucleic acid selection elements, such as a computer, database with nucleic acid sequences of interest, sequence alignment software, and oligonucleotide selection software. Suitable alignment algorithms, e.g., BLAST and others are discussed, supra. However, sequence alignment is optionally achieved manually. Once sequences to be synthesized, e.g., gap nucleic acids or split gene sequences, are selected, they can be converted into lines of character string information in data sets in a computer corresponding to the desired nucleic acids to be obtained.

The system also includes a user interface allowing a user to selectively view one or more sequence database programs for aligning and manipulating sequences. In addition, standard text manipulation software such as word processing software (e.g., Microsoft Word™ or Corel Wordperfect™) and database software (e.g., spreadsheet software such as Microsoft Excel™, Corel Quattro Pro™, or database programs such as Microsoft Access™ or Paradox™) can be used in conjunction with a user interface (e.g., a GUI in a standard operating system such as a Windows, Macintosh or Linux system) to manipulate strings of characters. As noted, specialized alignment software such as BLAST can also be included.

Additional software can be included, such as, components for ordering the selected nucleic acid sequences, and/or directing synthesis of such sequences by an operably linked automated synthesizer. In this case, the character string information in the output of an integrated computer directs the robotic arm of the automated synthesizer to perform the steps necessary to synthesize the desired polynucleotide sequences.

Although the integrated system elements of the invention optionally include any of the above components to facilitate, e.g., high-throughput recombination and selection. It will be appreciated that these high-throughput recombination elements can be in systems separate from those for performing selection assays, or as discussed, the two can be integrated.

Modifications can be made to the method and materials as hereinbefore described without departing from the spirit or scope of the invention as claimed, and the invention can be put to a number of different uses, including:

The use of an integrated system to select, e.g., non-overlapping gene sequences and gap nucleic acids, and to test recombined non-overlapping sequences for activity, including in an iterative process.

An assay, kit or system utilizing a use of any one of the selection strategies, materials, components, methods or substrates hereinbefore described. Kits will optionally additionally comprise instructions for performing methods or assays, packaging materials, one or more containers which contain assay, device or system components, or the like.

In an additional aspect, the present invention provides kits embodying the methods and apparatus herein. Kits of the invention optionally comprise one or more of the following: (1) a non-overlapping gene sequence recombination component as described herein; (2) instructions for practicing the methods described herein, and/or for operating the nucleic acid sequencing, synthesis, or recombined nucleic acid selection procedures herein; (3) one or more assay component(s); (4) a container for holding nucleic acids or enzymes, other nucleic acids, transgenic plants, animals, cells, or the like and, (5) packaging materials.

In a further aspect, the present invention provides for the use of any component or kit herein, for the practice of any method or assay herein, and/or for the use of any apparatus or kit to practice any assay or method herein.

While the foregoing invention has been described in some detail for purposes of clarity and understanding, it will be clear to one skilled in the art from a reading of this disclosure that various changes in form and detail can be made without departing from the true scope of the invention. For example, all the techniques, methods, compositions, apparatus and systems described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of unencrypting a trait encrypted gene sequence to provide at least one unencrypted RNA or polypeptide, the method comprising:

providing a first parental organism and a second parental organism, wherein the first parental organism comprises a first split gene sequence comprising a first subsequence of a genetic element, the second parental organism comprises a second split gene sequence comprising a second subsequence of the genetic element, and wherein the second split gene sequence is not present in the first parental organism and the first split gene sequence is not present in the second parental organism;

mating the first parental organism with the second parental organism to produce a progeny organism comprising the first split gene sequence and the second split gene sequence, wherein the split gene sequences are transcribed to provide a plurality of RNA segments; and trans-splicing at least two of the plurality of RNA segments together to provide at least one unencrypted RNA; or, alternately, translating the plurality of RNA segments to provide a plurality of polypeptide segments and trans-splicing at least two of the plurality of polypeptide segments together to provide at least one unencrypted polypeptide.

2. The method of claim 1, wherein the plurality of RNA segment comprises trans-splicing introns.

3. The method of claim 1, wherein the plurality of polypeptide segments comprises trans-splicing inteins.

4. The method of claim 1, the method further comprising selecting the progeny organism for at least one desired trait or property.

5. The method of claim 1, wherein the at least one unencrypted polypeptide is a full-length protein.

6. The method of claim 1, the method further comprising translating the at least one unencrypted RNA to provide a polypeptide encoded by the unencrypted RNA.

7. The method of claim 6, wherein the polypeptide encoded by the unencrypted RNA is a full-length protein.

8. The method of claim 1, wherein at least one of the split gene sequences is a cDNA.

9. The method of claim 1, wherein the parental organisms are selected from: animals, plants, fungi, and bacteria.

10. The method of claim 1, wherein the parental organisms are plants selected from the genera: Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Heterocallis, Nemesia, Pelargonium, Panicum, Pennisetum, Ranunculus, Senecio, Salpiglossis, Cucumis, Browaalia, Lolium, Malus, Apium, Gossypium, Vicia, Lathyrus, Lupinus, Pachyrhizus, Wisteria, and Stizolobium.

11. The method of claim 1, wherein the parental organisms are crop plants selected from the genera: Agrostis, Phleum, Dactylis, Sorghum, Setaria, Zea, Oryza, Triticum, Secale, Avena, Hordeum, Saccharum, Poa, Festuca, Stenotaphrum, Cynodon, Coix, Olyreae, Phareae, Glycine, Pisum, Cicer, Phaseolus, Lens, and Arachis.

12. The method of claim 1, wherein the parental organisms are plants selected from: corn, rice, cotton, soybean, sorghum, wheat, oats, barley, millet, sunflower, rapeseed, canola, peas, beans, lentils, peanuts, yam beans, cowpeas, velvet beans, clover, alfalfa, lupine, vetch, lotus, sweet clover, wisteria, and sweetpea.

13. The method of claim 1, wherein the parental organisms are yeast.

14. The method of claim 1, wherein:

the first split gene sequence is a first enhancer-linked split gene sequence, comprising a subsequence of the genetic element with a first enhancer sequence linked thereto;

the second split gene sequence is a second enhancer-linked split gene sequence, comprising a subsequence of the genetic element with a first enhancer sequence linked thereto;

the first parental organism comprises a first trans-acting transcription factor sequence that is unlinked to the first enhancer-linked split gene sequence; and the second parental organism comprises a second trans-acting transcription factor sequence that is unlinked to the second enhancer-linked split gene sequence.

15. The method of claim 14, wherein the progeny organism comprises the first enhancer-linked split gene sequence, the first trans-acting transcription factor sequence, the second enhancer-linked split gene sequence, and the second trans-acting transcription factor sequence, wherein the first and second enhancer-linked split gene sequences are transcribed to provide the plurality of RNA segments, wherein the first enhancer-linked split gene sequence is regulated by the second trans-acting transcription factor and the second enhancer-linked split gene sequence is regulated by the first trans-acting transcription factor.

16. The method of claim 15, the method further comprising selecting the progeny organism for a desired trait or property.

17. The method of claim 15, the method further comprising translating the at least one unencrypted RNA to provide a polypeptide encoded by the unencrypted RNA.

18. The method of claim 17, wherein the polypeptide encoded by the unencrypted RNA is a full-length protein.

19. The method of claim 15, wherein at least one of the enhancer-linked split gene sequences is a cDNA.

20. The method of claim 15, wherein at least one of the trans-acting transcription factor sequences is a cDNA.

21. The method of claim 15, wherein the parental organisms are selected from: animals, plants, fungi, and bacteria.

22. The method of claim 21, wherein the parental organisms are plants selected from the genera: Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Heterocallis, Nemesia, Pelargonium, Panicum, Pennisetum, Ranunculus, Senecio, Salpiglossis, Cucumis, Browaalia, Lolium, Malus, Apium, Gossypium, Vicia, Lathyrus, Lupinus, Pachyrhizus, Wisteria, and Stizolobium.

23. The method of claim 21, wherein the parental organisms are crop plant selected from the genera: Agrostis, Phleum, Dactylis, Sorghum, Setaria, Zea, Oryza, Triticum, Secale, Avena, Hordeum, Saccharum, Poa, Festuca, Stenotaphrum, Cynodon, Coix, Olyreae, Phareae, Glycine, Pisum, Cicer, Phaseolus, Lens, and Arachis.

24. The method of claim 21, wherein the parental organisms are plants selected from: corn, rice, cotton, soybean, sorghum, wheat, oats, barley, millet, sunflower, rapeseed, canola, peas, beans, lentils, peanuts, yam beans, cowpeas, velvet beans, clover, alfalfa, lupine, vetch, lotus, sweet clover, wisteria, and sweetpea.

25. The method of claim 21, wherein the parental organisms are yeast.

26. The method of claim 1, wherein:

the first split gene sequence comprises a first subsequence of a toxic genetic element; and the second split gene sequence comprises a second subsequence of the toxic genetic element.

27. The method of claim 26, wherein the first and second split gene sequences are expressed in the progeny organism to produce a plurality of polypeptide segments, wherein at least two of the plurality of polypeptide sequences are spliced together to provide a toxic polypeptide, wherein the toxic polypeptide renders the progeny organism incapable of reproducing when the progeny organism is male.

28. The method of claim 27, wherein the progeny organism is capable of reproducing when the progeny organism is female.

29. The method of claim 28, wherein the progeny organism reproduces as a female to produce a hybrid progeny organism, wherein the toxic genetic element is not expressed in the hybrid progeny organism.

30. The method of claim 26, wherein the first and second split gene sequences are expressed in the progeny organism to produce a plurality of polypeptide segments, wherein at least two of the plurality of polypeptide sequences are spliced together to provide a toxic polypeptide, wherein the toxic polypeptide renders the progeny organism incapable of reproducing when the progeny organism is female.

31. The method of claim 30, wherein the progeny organism is capable of reproducing when the progeny organism is male.

32. The method of claim 31, wherein the progeny organism reproduces as a male to produce a hybrid progeny organism, wherein the toxic genetic element is not expressed in the hybrid progeny organism.

33. The method of claim 26, wherein at least one of the toxic split gene sequences is a cDNA.

34. A method of unencrypting a trait encrypted gene sequence to provide at least one unencrypted RNA or polypeptide, the method comprising:

providing a host organism and a vector, wherein the host organism comprises a first split gene sequence comprising a first subsequence of a genetic element, the vector comprises a second split gene sequence comprising a second subsequence of the genetic element, and wherein the second split gene sequence is not present in the host organism and the first split gene sequence is not present in the vector;

infecting the host organism with the vector to produce an infected organism comprising the first split gene sequence and the second split gene sequence, wherein the split gene sequences are transcribed to provide a plurality of RNA segments; and trans-splicing at least two of the plurality of RNA segments together to provide at least one unencrypted RNA; or, alternately, translating the plurality of RNA segments to provide a plurality of polypeptide segments and trans-splicing at least two of the plurality of polypeptide segments together to provide at least one unencrypted polypeptide.

35. The method of claim 34, the method further comprising selecting the at least one unencrypted RNA.

36. The method of claim 34, the method further comprising translating the at least one unencrypted RNA to provide a polypeptide encoded by the unencrypted RNA.

37. The method of claim 36, wherein the polypeptide encoded by the unencrypted RNA is a full-length protein.

38. The method of claim 36, the method further comprising selecting the polypeptide encoded by the unencrypted RNA for at least one desired trait or property.

39. The method of claim 34, the method further comprising selecting the at least one unencrypted polypeptide for at least one desired trait or property.

40. The method of claim 34, wherein at least one of the split gene sequences is a cDNA.

41. The method of claim 34, wherein the vector comprises a virus.

* * * * *